United States Patent
Lee et al.

(10) Patent No.: US 9,771,604 B2
(45) Date of Patent: Sep. 26, 2017

(54) GENETICALLY ENGINEERED YEAST CELL WITH ENHANCED EDC ACTIVITY AND CAPABILITY OF PRODUCING LACTATE, METHOD OF PRODUCING THE YEAST CELL, AND METHOD OF PRODUCING LACTATE BY USING THE YEAST CELL

(71) Applicant: Samsung Electronics Co., Ltd., Suwon-si, Gyeonggi-do (KR)

(72) Inventors: Wooyong Lee, Hwaseong-si (KR); Soyoung Lee, Daejeon (KR); Jiyoon Song, Seoul (KR); Kwangmyung Cho, Seongnam-si (KR)

(73) Assignee: SAMSUN ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/845,009

(22) Filed: Sep. 3, 2015

(65) Prior Publication Data

US 2016/0068874 A1   Mar. 10, 2016

(30) Foreign Application Priority Data

Sep. 5, 2014   (KR) .................. 10-2014-0119374

(51) Int. Cl.
| | |
|---|---|
| *C12P 7/56* | (2006.01) |
| *C12N 1/19* | (2006.01) |
| *C07K 14/395* | (2006.01) |
| *C12N 15/52* | (2006.01) |

(52) U.S. Cl.
CPC .............. *C12P 7/56* (2013.01); *C07K 14/395* (2013.01); *C12N 15/52* (2013.01)

(58) Field of Classification Search
None
See application file for complete search history.

(56) References Cited

U.S. PATENT DOCUMENTS

| 7,534,597 B2 | 5/2009 | Hause et al. |
| 2005/0120394 A1 | 6/2005 | Saitoh et al. |
| 2011/0104769 A1 | 5/2011 | Porro et al. |
| 2013/0244243 A1 | 9/2013 | Matsuyama et al. |

FOREIGN PATENT DOCUMENTS

KR   2014-0050226 A   4/2014

OTHER PUBLICATIONS

Wu et al., Appl. Microbiol. Biotechnol. 98:1055-1063, Dec. 2013.*
Neef et al., Mol. Microbiol. 73:1032-1042, 2009.*
UniProt Database Accession No. P40023, Jul. 2014, 3 pages.*
Adachi et al., J. Ferment. Bioengineer. 86:284-289, 1998.*
GenBank Accession No. NP_776524, Feb. 2014, 1 page.*
Kim et al., J. Microbiol. 50:544-546, 2012.*
Schwartz et al., RNA 9:239-251, 2003.*
Mourier et al., Biochim. Biophys. Acta 1777:1283-1288, 2008.*
Abbott et al., "Physiological and Transcriptional Responses to High Concentrations of Lactic Acid in Anaerobic Chemostat Cultures of *Saccharomyces cerevisiae*", *Applied and Environmental Microbiology*, 74(18): 5759-5768 (2008).

* cited by examiner

*Primary Examiner* — David J Steadman
(74) *Attorney, Agent, or Firm* — Leydig, Voit & Mayer, Ltd.

(57) ABSTRACT

A genetically engineered yeast cell with enhanced activity of an EDC protein compared to that of a parent cell and capability of producing lactate, a method of producing the yeast cell, and a method of producing lactate by using the yeast cell.

17 Claims, 3 Drawing Sheets

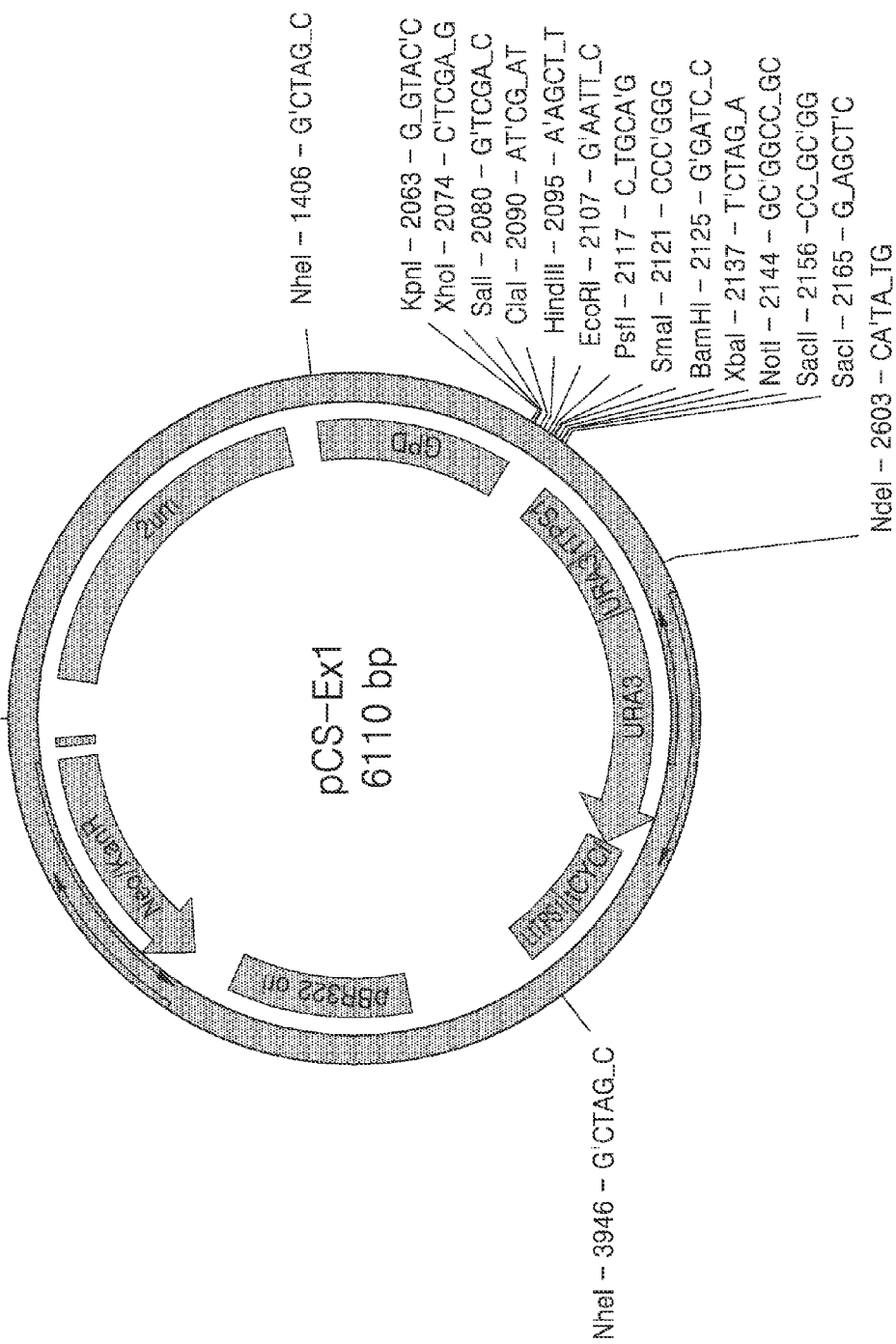

SEQUENCE LISTING

```
<160> NUMBER OF SEQ ID NOS: 67

<210> SEQ ID NO 1
<211> LENGTH: 145
<212> TYPE: PRT
<213> ORGANISM: Saccharomyces cerevisiae

<400> SEQUENCE: 1

Met Gly Ser Glu Thr Lys His Ser Ala Lys Val Lys Ile Val Thr Arg
 1               5                  10                  15

Glu Ser Pro Pro Ser Ala Lys Glu His Met Arg Pro Thr Lys Thr Gln
            20                  25                  30

Ile Leu Val Pro Pro Thr Gln Ser Leu Pro Asn Gly Lys Lys Pro Asn
        35                  40                  45

Phe Gly Lys Ser Thr Lys Gln Arg Arg Glu Pro Arg Glu Arg Thr Ser
    50                  55                  60

Lys Thr Gly His Glu Asp Asp Lys Ala Thr Met Val Thr Val Asn Ile
65                  70                  75                  80
```

```
Asp Ala Phe Leu His Asp Lys Ala Pro Lys Lys Ser Cys Lys Tyr
            85                  90                  95

Lys Lys Lys Lys Thr Arg Gln Tyr Gln Asp Arg Ala Ala Ala Ser Ile
            100                 105                 110

Asp Ser Lys Pro His Val Ala Gly His Thr Ala Phe Gly Ala Ser
            115                 120                 125

Phe Thr Thr Asp Ile Pro His Glu Ala Ala Leu Pro Lys Pro Ser Phe
        130                 135                 140

Val
145

<210> SEQ ID NO 2
<211> LENGTH: 438
<212> TYPE: DNA
<213> ORGANISM: Saccharomyces cerevisiae

<400> SEQUENCE: 2
atgggttccg agacaaaaca ttctgcaaaa gtcaagattg tcacaaggga aagtcctcct      60
tccgccaagg agcacatgcg ccccactaaa actcaaatat tagttccacc gacgcagagt     120
ttgcccaatg gcaagaaacc aaacttcggt aagtctacaa acagcggcg agaacctagg      180 gaacgcacct cgaagacggg acacgaggac gataaggcaa cgatggtcac tgttaacata     240
gatgccttcc tacatgataa ggcccctaaa aaaaaatcgt gcaaatacaa gaagaagaaa     300
acgagacagt accaggatag ggcggcggcg tcgatcgatt cgaaaccgca cgtagctggt     360
catacggcct ttgccggtgc ttcgttcaca acagatatcc cacatgaggc agcgctaccc     420
aaacctagtt ttgtttga                                                   438

<210> SEQ ID NO 3
<211> LENGTH: 175
<212> TYPE: PRT
<213> ORGANISM: Saccharomyces cerevisiae

<400> SEQUENCE: 3

Met Ser Thr Asp Thr Met Tyr Phe Asn Ser Ser Arg Leu Leu Pro Ser
 1                   5                   10                  15

Ala Gly Arg Asn Lys Thr Asn Asn Leu Ile Lys Gln Lys Thr Arg Asn
            20                  25                  30

Asn Arg Ala Arg Gly Asn Ala Ala Lys Asn Ala Asn Asn Asn Tyr
            35                  40                  45

Ile Thr Asp Ile Pro Pro Pro Gln Thr Leu Pro Asn Gly Gln Lys Pro
        50                  55                  60

Asn Phe Gly His Ser Ser Asn Lys Lys Pro Ser Phe Asn Gln Lys Lys
65                  70                  75                  80

His Ser Pro Pro Ser Ser Pro Ser Ser Thr Thr Thr Leu Gly Lys Lys
                85                  90                  95

Asn Arg Gln Asn Asn Lys Glu Thr Pro Arg Gln Asn Asn Lys Asp Asp
            100                 105                 110

Thr Arg Leu Leu Ser Gln Asn Leu Lys Asn Leu Leu Asn Gln Lys
            115                 120                 125

Gln Ser Pro His Gly Ser Gln Gly Ile Ile Pro Met Gly Cys Asn Gly
            130                 135                 140

Ser Ala Lys Lys Leu Ser His Ser Tyr Ala Gly Ser Thr Phe Ala Thr
145                 150                 155                 160

Asn Gly Pro Arg Glu Ala Lys Asn Leu Pro Lys Pro Ser Phe Leu
```

<210> SEQ ID NO 4
<211> LENGTH: 528
<212> TYPE: DNA
<213> ORGANISM: Saccharomyces cerevisiae

<400> SEQUENCE: 4

```
atgtcgacgg ataccatgta tttcaacagc tccaggctgt tgccatcggc tggcaggaac      60
aagacaaata atctaatcaa acaaaaaact agaaataatc gtgcgagggg aaatgctgct     120
aagaacgcca ataataacaa ctatatcaca gatataccac ctcctcaaac tcttcctaac     180
ggtcagaaac ctaacttcgg ccattcttcc aacaagaaac catcatttaa tcaaaagaag     240
cactctccac cttcttcccc ttcctctaca actactttag gtaaaaaaaa cagacagaat     300
aataagaaa cgccacgaca gaacaacaaa gatgatactc gtttactgag tcagaaccta      360
aagaatctgc ttctgaacca gaaacaatcc ccgcatggct ctcaagggat aataccaatg     420
ggttgtaatg gcagtgccaa aaaactcagt cactcttatg caggctccac tttcgccact     480
aatggtccaa gggaggctaa aaacttgccc aaaccaagtt ttttataa                  528
```

<210> SEQ ID NO 5
<211> LENGTH: 563
<212> TYPE: PRT
<213> ORGANISM: Saccharomyces cerevisiae

<400> SEQUENCE: 5

Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Thr
    130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Ala Leu Val
        195                 200                 205

Lys Asp Ala Lys Asn Pro Val Ile Leu Ala Asp Ala Cys Cys Ser Arg
    210                 215                 220

His Asp Val Lys Ala Glu Thr Lys Lys Leu Ile Asp Leu Thr Gln Phe

Pro Ala Phe Val Thr Pro Met Gly Lys Gly Ser Ile Asp Glu Gln His
            245                 250                 255

Pro Arg Tyr Gly Gly Val Tyr Val Gly Thr Leu Ser Lys Pro Glu Val
        260                 265                 270

Lys Glu Ala Val Glu Ser Ala Asp Leu Ile Leu Ser Val Gly Ala Leu
    275                 280                 285

Leu Ser Asp Phe Asn Thr Gly Ser Phe Ser Tyr Ser Tyr Lys Thr Lys
290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
            340                 345                 350

Thr Pro Ala Asn Ala Ala Val Pro Ala Ser Thr Pro Leu Lys Gln Glu
        355                 360                 365

Trp Met Trp Asn Gln Leu Gly Asn Phe Leu Gln Glu Gly Asp Val Val
    370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
            420                 425                 430

Asp Pro Lys Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
                485                 490                 495

Ser Leu Leu Pro Thr Phe Gly Ala Lys Asp Tyr Glu Thr His Arg Val
            500                 505                 510

Ala Thr Thr Gly Glu Trp Asp Lys Leu Thr Gln Asp Lys Ser Phe Asn
        515                 520                 525

Asp Asn Ser Lys Ile Arg Met Ile Glu Ile Met Leu Pro Val Phe Asp
    530                 535                 540

Ala Pro Gln Asn Leu Val Glu Gln Ala Lys Leu Thr Ala Ala Thr Asn
545                 550                 555                 560

Ala Lys Gln

<210> SEQ ID NO 6
<211> LENGTH: 1692
<212> TYPE: DNA
<213> ORGANISM: Saccharomyces cerevisiae

<400> SEQUENCE: 6
atgtctgaaa ttactttggg taaatatttg ttcgaaagat aaagcaagt caacgttaac      60 accgttttcg gtttgccagg tgacttcaac ttgtccttgt ggacaagat ctacgaagtt    120 gaaggtatga gatgggctgg taacgccaac gaattgaacg ctgcttacgc cgctgatggt    180
tacgctcgta tcaagggtat gtcttgtatc atcaccacct tcggtgtcgg tgaattgtct    240

```
gctttgaacg gtattgccgg ttcttacgct gaacacgtcg gtgttttgca cgttgttggt    300
gtcccatcca tctctgctca agctaagcaa ttgttgttgc accacacctt gggtaacggt    360
gacttcactg ttttccacag aatgtctgcc aacatttctg aaaccactgc tatgatcact    420
gacattgcta ccgccccagc tgaaattgac agatgtatca gaaccactta cgtcacccaa    480
agaccagtct acttaggttt gccagctaac ttggtcgact gaacgtccc agctaagttg    540
ttgcaaactc caattgacat gtctttgaag ccaaacgatg ctgaatccga aaaggaagtc    600
attgacacca tcttggcttt ggtcaaggat gctaagaacc cagttatctt ggctgatgct    660
tgttgttcca gacacgacgt caaggctgaa actaagaagt tgattgactt gactcaattc    720
ccagctttcg tcaccccaat gggtaagggt tccattgacg aacaacaccc aagatacggt    780
ggtgtttacg tcggtacctt gtccaagcca gaagttaagg aagccgttga atctgctgac    840
ttgattttgt ctgtcggtgc tttgttgtct gatttcaaca ccggttcttt ctcttactct    900
tacaagacca gaacattgt cgaattccac tccgaccaca tgaagatcag aaacgccact    960
ttcccaggtg tccaaatgaa attcgttttg caaaagttgt tgaccactat tgctgacgcc   1020
gctaagggtt acaagccagt tgctgtccca gctagaactc cagctaacgc tgctgtccca   1080
gcttctaccc cattgaagca agaatggatg tggaaccaat gggtaacttc cttgcaagaa   1140
ggtgatgttg tcattgctga aaccggtacc tccgctttcg gtatcaacca aaccactttc   1200
ccaaacaaca cctacggtat ctctcaagtc ttatggggtt ccattggttt caccactggt   1260
gctaccttgg gtgctgcttt cgctgctgaa gaaattgatc aaagaagag agttatctta   1320
ttcattggtg acggttcttt gcaattgact gttcaagaaa tctccaccat gatcagatgg   1380
ggcttgaagc atacttgtt cgtcttgaac aacgatggtt acaccattga aaagttgatt   1440
cacggtccaa aggctcaata acgaaatt caaggttggg accacctatc cttgttgcca   1500
actttcggtg ctaaggacta tgaaaccac agagtcgcta ccaccggtga atgggacaag   1560
ttgacccaag acaagtcttt caacgacaac tctaagatca gaatgattga atcatgttg   1620
ccagtcttcg atgctccaca aaacttggtt gaacaagcta agttgactgc tgctaccaac   1680
gctaagcaat aa                                                       1692
```

<210> SEQ ID NO 7
<211> LENGTH: 591
<212> TYPE: PRT
<213> ORGANISM: Saccharomyces cerevisiae

<400> SEQUENCE: 7

```
Met Leu Lys Tyr Lys Pro Leu Leu Lys Ile Ser Lys Asn Cys Glu Ala
 1               5                  10                  15

Ala Ile Leu Arg Ala Ser Lys Thr Arg Leu Asn Thr Ile Arg Ala Tyr
            20                  25                  30

Gly Ser Thr Val Pro Lys Ser Lys Ser Phe Glu Gln Asp Ser Arg Lys
        35                  40                  45

Arg Thr Gln Ser Trp Thr Ala Leu Arg Val Gly Ala Ile Leu Ala Ala
    50                  55                  60

Thr Ser Ser Val Ala Tyr Leu Asn Trp His Asn Gly Gln Ile Asp Asn
65                  70                  75                  80

Glu Pro Lys Leu Asp Met Asn Lys Gln Lys Ile Ser Pro Ala Glu Val
                85                  90                  95

Ala Lys His Asn Lys Pro Asp Asp Cys Trp Val Val Ile Asn Gly Tyr
            100                 105                 110
```

-continued

Val Tyr Asp Leu Thr Arg Phe Leu Pro Asn His Pro Gly Gly Gln Asp
        115                 120                 125

Val Ile Lys Phe Asn Ala Gly Lys Asp Val Thr Ala Ile Phe Glu Pro
130                 135                 140

Leu His Ala Pro Asn Val Ile Asp Lys Tyr Ile Ala Pro Glu Lys Lys
145                 150                 155                 160

Leu Gly Pro Leu Gln Gly Ser Met Pro Pro Glu Leu Val Cys Pro Pro
                165                 170                 175

Tyr Ala Pro Gly Glu Thr Lys Glu Asp Ile Ala Arg Lys Glu Gln Leu
            180                 185                 190

Lys Ser Leu Leu Pro Pro Leu Asp Asn Ile Ile Asn Leu Tyr Asp Phe
        195                 200                 205

Glu Tyr Leu Ala Ser Gln Thr Leu Thr Lys Gln Ala Trp Ala Tyr Tyr
    210                 215                 220

Ser Ser Gly Ala Asn Asp Glu Val Thr His Arg Glu Asn His Asn Ala
225                 230                 235                 240

Tyr His Arg Ile Phe Phe Lys Pro Lys Ile Leu Val Asp Val Arg Lys
                245                 250                 255

Val Asp Ile Ser Thr Asp Met Leu Gly Ser His Val Asp Val Pro Phe
            260                 265                 270

Tyr Val Ser Ala Thr Ala Leu Cys Lys Leu Gly Asn Pro Leu Glu Gly
        275                 280                 285

Glu Lys Asp Val Ala Arg Gly Cys Gly Gln Gly Val Thr Lys Val Pro
    290                 295                 300

Gln Met Ile Ser Thr Leu Ala Ser Cys Ser Pro Glu Glu Ile Ile Glu
305                 310                 315                 320

Ala Ala Pro Ser Asp Lys Gln Ile Gln Trp Tyr Gln Leu Tyr Val Asn
                325                 330                 335

Ser Asp Arg Lys Ile Thr Asp Asp Leu Val Lys Asn Val Glu Lys Leu
            340                 345                 350

Gly Val Lys Ala Leu Phe Val Thr Val Asp Ala Pro Ser Leu Gly Gln
        355                 360                 365

Arg Glu Lys Asp Met Lys Leu Lys Phe Ser Asn Thr Lys Ala Gly Pro
    370                 375                 380

Lys Ala Met Lys Lys Thr Asn Val Glu Glu Ser Gln Gly Ala Ser Arg
385                 390                 395                 400

Ala Leu Ser Lys Phe Ile Asp Pro Ser Leu Thr Trp Lys Asp Ile Glu
                405                 410                 415

Glu Leu Lys Lys Lys Thr Lys Leu Pro Ile Val Ile Lys Gly Val Gln
            420                 425                 430

Arg Thr Glu Asp Val Ile Lys Ala Ala Glu Ile Gly Val Ser Gly Val
        435                 440                 445

Val Leu Ser Asn His Gly Gly Arg Gln Leu Asp Phe Ser Arg Ala Pro
    450                 455                 460

Ile Glu Val Leu Ala Glu Thr Met Pro Ile Leu Glu Gln Arg Asn Leu
465                 470                 475                 480

Lys Asp Lys Leu Glu Val Phe Val Asp Gly Gly Val Arg Arg Gly Thr
                485                 490                 495

Asp Val Leu Lys Ala Leu Cys Leu Gly Ala Lys Gly Val Gly Leu Gly
            500                 505                 510

Arg Pro Phe Leu Tyr Ala Asn Ser Cys Tyr Gly Arg Asn Gly Val Glu
        515                 520                 525

```
Lys Ala Ile Glu Ile Leu Arg Asp Glu Ile Glu Met Ser Met Arg Leu
        530                 535                 540

Leu Gly Val Thr Ser Ile Ala Glu Leu Lys Pro Asp Leu Leu Asp Leu
545                 550                 555                 560

Ser Thr Leu Lys Ala Arg Thr Val Gly Val Pro Asn Asp Val Leu Tyr
                565                 570                 575

Asn Glu Val Tyr Glu Gly Pro Thr Leu Thr Glu Phe Glu Asp Ala
                580                 585                 590

<210> SEQ ID NO 8
<211> LENGTH: 1776
<212> TYPE: DNA
<213> ORGANISM: Saccharomyces cerevisiae

<400> SEQUENCE: 8
atgctaaaat acaaaccttt actaaaaatc tcgaagaact gtgaggctgc tatcctcaga      60
gcgtctaaga ctagattgaa cacaatccgc gcgtacggtt ctaccgttcc aaaatccaag     120
tcgttcgaac aagactcaag aaaacgcaca cagtcatgga ctgccttgag agtcggtgca     180
attctagccg ctactagttc cgtggcgtat ctaaactggc ataatggcca aatagacaac     240
gagccgaaac tggatatgaa taaacaaaag atttcgcccg ctgaagttgc caagcataac     300
aagcccgatg attgttgggt tgtgatcaat ggttacgtat acgacttaac gcgattccta     360
ccaaatcatc caggtgggca ggatgttatc aagtttaacg ccgggaaaga tgtcactgct     420
atttttgaac cactacatgc tcctaatgtc atcgataagt atatagctcc cgagaaaaaa     480
ttgggtcccc ttcaaggatc catgcctcct gaacttgtct gtcctcctta tgctcctggt     540
gaaactaagg aagatatcgc tagaaaagaa caactaaaat cgctgctacc tcctctagat     600
aatattatta acctttacga ctttgaatac ttggcctctc aaactttgac taaacaagcg     660
tgggcctact attcctccgg tgctaacgac gaagttactc acagagaaaa ccataatgct     720
tatcatagga ttttttttcaa accaaagatc cttgtagatg tacgcaaagt agacatttca     780
actgacatgt tgggttctca tgtggatgtt cccttctacg tgtctgctac agctttgtgt     840
aaactgggaa acccccttaga aggtgaaaaa gatgtcgcca gaggttgtgg ccaaggtgtg     900
acaaaagtcc cacaaatgat atctactttg gcttcatgtt cccctgagga aattattgaa     960
gcagcaccct ctgataaaca aattcaatgg taccaactat atgttaactc tgatagaaag    1020
atcactgatg atttggttaa aaatgtagaa aagctgggtg taaaggcatt atttgtcact    1080
gtggatgctc caagtttagg tcaaagagaa aaagatatga gctgaaaatt ttccaataca    1140
aaggctggtc caaaagcgat gaagaaaact aatgtagaag aatctcaagg tgcttcgaga    1200
gcgttatcaa agtttattga cccctctttg acttggaaag atatagaaga gttgaagaaa    1260
aagacaaaac tacctattgt tatcaaaggt gttcaacgta ccgaagatgt tatcaaagca    1320
gcagaaatcg gtgtaagtgg ggtggttcta tccaatcatg gtggtagaca attagatttt    1380
tcaagggctc ccattgaagt cctggctgaa accatgccaa tcctggaaca acgtaacttg    1440
aaggataagt tggaagtttt cgtggacggt ggtgttcgtc gtggtacaga tgtcttgaaa    1500
gcgttatgtc taggtgctaa aggtgttggt ttgggtagac cattcttgta tcgaactca    1560 tgctatggtc gtaatggtgt tgaaaaagcc attgaaattt aagagatga aattgaaatg    1620 tctatgagac tattaggtgt tactagcatt gcggaattga gcctgatct tttagatcta    1680 tcaacactaa aggcaagaac agttggagta ccaaacgacg tgctgtataa tgaagtttat    1740
gagggaccta cttttaacaga atttgaggat gcatga                           1776
```

<210> SEQ ID NO 9
<211> LENGTH: 391
<212> TYPE: PRT
<213> ORGANISM: Saccharomyces cerevisiae

<400> SEQUENCE: 9

```
Met Ser Ala Ala Ala Asp Arg Leu Asn Leu Thr Ser Gly His Leu Asn
 1               5                  10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
```

```
                  370              375             380
Glu Leu Asp Leu His Glu Asp
385                 390

<210> SEQ ID NO 10
<211> LENGTH: 1176
<212> TYPE: DNA
<213> ORGANISM: Saccharomyces cerevisiae

<400> SEQUENCE: 10
atgtctgctg ctgctgatag attaaactta acttccggcc acttgaatgc tggtagaaag      60
agaagttcct cttctgtttc tttgaaggct gccgaaaagc ctttcaaggt tactgtgatt     120
ggatctggta actggggtac tactattgcc aaggtggttg ccgaaaattg taagggatac     180
ccagaagttt tcgctccaat agtacaaatg tgggtgttcg aagaagagat caatggtgaa     240
aaattgactg aaatcataaa tactagacat caaaacgtga atacttgcc tggcatcact      300 ctacccgaca atttggttgc taatccagac ttgattgatt cagtcaagga tgtcgacatc     360
atcgttttca acattccaca tcaattttg ccccgtatct gtagccaatt gaaaggtcat      420
gttgattcac acgtcagagc tatctcctgt ctaaagggtt ttgaagttgg tgctaaaggt     480
gtccaattgc tatcctctta catcactgag gaactaggta ttcaatgtgg tgctctatct     540
ggtgctaaca ttgccaccga agtcgctcaa gaacactggt ctgaaacaac agttgcttac     600
cacattccaa aggatttcag aggcgagggc aaggacgtcg accataaggt tctaaaggcc     660
ttgttccaca gaccttactt ccacgttagt gtcatcgaag atgttgctgg tatctccatc     720
tgtggtgctt tgaagaacgt tgttgcctta ggttgtggtt tcgtcgaagg tctaggctgg     780
ggtaacaacg cttctgctgc catccaaaga gtcggtttgg gtgagatcat cagattcggt     840
caaatgtttt tcccagaatc tagagaagaa acatactacc aagagtctgc tggtgttgct     900
gatttgatca ccacctgcgc tggtggtaga aacgtcaagg ttgctaggct aatggctact     960
tctggtaagg acgcctggga atgtgaaaag gagttgttga atggccaatc cgctcaaggt    1020
ttaattacct gcaaagaagt tcacgaatgg ttggaaacat gtggctctgt cgaagacttc    1080
ccattatttg aagccgtata ccaaatcgtt tacaacaact acccaatgaa gaacctgccg    1140
gacatgattg aagaattaga tctacatgaa gattag                              1176

<210> SEQ ID NO 11
<211> LENGTH: 587
<212> TYPE: PRT
<213> ORGANISM: Saccharomyces cerevisiae

<400> SEQUENCE: 11

Met Leu Trp Lys Arg Thr Cys Thr Arg Leu Ile Lys Pro Ile Ala Gln
  1               5                  10                  15

Pro Arg Gly Arg Leu Val Arg Arg Ser Cys Tyr Arg Tyr Ala Ser Thr
                 20                  25                  30

Gly Thr Gly Ser Thr Asp Ser Ser Ser Gln Trp Leu Lys Tyr Ser Val
             35                  40                  45

Ile Ala Ser Ser Ala Thr Leu Phe Gly Tyr Leu Phe Ala Lys Asn Leu
         50                  55                  60

Tyr Ser Arg Glu Thr Lys Glu Asp Leu Ile Glu Lys Leu Glu Met Val
 65                  70                  75                  80

Lys Lys Ile Asp Pro Val Asn Ser Thr Leu Lys Leu Ser Ser Leu Asp
                 85                  90                  95
```

```
Ser Pro Asp Tyr Leu His Asp Pro Val Lys Ile Asp Lys Val Val Glu
                100                 105                 110
Asp Leu Lys Gln Val Leu Gly Asn Lys Pro Glu Asn Tyr Ser Asp Ala
            115                 120                 125
Lys Ser Asp Leu Asp Ala His Ser Asp Thr Tyr Phe Asn Thr His His
130                 135                 140
Pro Ser Pro Glu Gln Arg Pro Arg Ile Ile Leu Phe Pro His Thr Thr
145                 150                 155                 160
Glu Glu Val Ser Lys Ile Leu Lys Ile Cys His Asp Asn Asn Met Pro
                165                 170                 175
Val Val Pro Phe Ser Gly Gly Thr Ser Leu Glu Gly His Phe Leu Pro
            180                 185                 190
Thr Arg Ile Gly Asp Thr Ile Thr Val Asp Leu Ser Lys Phe Met Asn
        195                 200                 205
Asn Val Val Lys Phe Asp Lys Leu Asp Leu Asp Ile Thr Val Gln Ala
            210                 215                 220
Gly Leu Pro Trp Glu Asp Leu Asn Asp Tyr Leu Ser Asp His Gly Leu
225                 230                 235                 240
Met Phe Gly Cys Asp Pro Gly Pro Gly Ala Gln Ile Gly Gly Cys Ile
                245                 250                 255
Ala Asn Ser Cys Ser Gly Thr Asn Ala Tyr Arg Tyr Gly Thr Met Lys
            260                 265                 270
Glu Asn Ile Ile Asn Met Thr Ile Val Leu Pro Asp Gly Thr Ile Val
        275                 280                 285
Lys Thr Lys Lys Arg Pro Arg Lys Ser Ser Ala Gly Tyr Asn Leu Asn
        290                 295                 300
Gly Leu Phe Val Gly Ser Glu Gly Thr Leu Gly Ile Val Thr Glu Ala
305                 310                 315                 320
Thr Val Lys Cys His Val Lys Pro Lys Ala Glu Thr Val Ala Val Val
                325                 330                 335
Ser Phe Asp Thr Ile Lys Asp Ala Ala Ala Cys Ala Ser Asn Leu Thr
            340                 345                 350
Gln Ser Gly Ile His Leu Asn Ala Met Glu Leu Leu Asp Glu Asn Met
        355                 360                 365
Met Lys Leu Ile Asn Ala Ser Glu Ser Thr Asp Arg Cys Asp Trp Val
        370                 375                 380
Glu Lys Pro Thr Met Phe Phe Lys Ile Gly Gly Arg Ser Pro Asn Ile
385                 390                 395                 400
Val Asn Ala Leu Val Asp Glu Val Lys Ala Val Ala Gln Leu Asn His
                405                 410                 415
Cys Asn Ser Phe Gln Phe Ala Lys Asp Asp Asp Glu Lys Leu Glu Leu
            420                 425                 430
Trp Glu Ala Arg Lys Val Ala Leu Trp Ser Val Leu Asp Ala Asp Lys
        435                 440                 445
Ser Lys Asp Lys Ser Ala Lys Ile Trp Thr Thr Asp Val Ala Val Pro
450                 455                 460
Val Ser Gln Phe Asp Lys Val Ile His Glu Thr Lys Lys Asp Met Gln
465                 470                 475                 480
Ala Ser Lys Leu Ile Asn Ala Ile Val Gly His Ala Gly Asp Gly Asn
                485                 490                 495
Phe His Ala Phe Ile Val Tyr Arg Thr Pro Glu Glu His Glu Thr Cys
            500                 505                 510
Ser Gln Leu Val Asp Arg Met Val Lys Arg Ala Leu Asn Ala Glu Gly
```

```
                515                 520                 525
Thr Cys Thr Gly Glu His Gly Val Gly Ile Gly Lys Arg Glu Tyr Leu
    530                 535                 540

Leu Glu Glu Leu Gly Glu Ala Pro Val Asp Leu Met Arg Lys Ile Lys
545                 550                 555                 560

Leu Ala Ile Asp Pro Lys Arg Ile Met Asn Pro Asp Lys Ile Phe Lys
                565                 570                 575

Thr Asp Pro Asn Glu Pro Ala Asn Asp Tyr Arg
            580                 585

<210> SEQ ID NO 12
<211> LENGTH: 1764
<212> TYPE: DNA
<213> ORGANISM: Saccharomyces cerevisiae

<400> SEQUENCE: 12
```

| | | | | | |
|---|---|---|---|---|---|
| atgttgtgga | agcgtacttg | cacaaggcta | ataaagccta | ttgcacaacc | tagaggaagg | 60 |
| ctggtgagaa | gatcatgcta | cagatacgcc | tcaacaggca | caggcagcac | cgacagcagc | 120 |
| agccagtggt | taaaatactc | tgtcatcgcc | tcttcagcta | ctctattcgg | ttatttgttc | 180 |
| gctaagaacc | tctattctag | ggagactaag | gaagatttga | tagagaagct | ggaaatggtc | 240 |
| aaaaagatcg | acccagtaaa | ttctacgtta | agctgtcct | cattggactc | accagactat | 300 |
| ttgcacgacc | cggttaagat | cgataaggtt | gttgaggacc | tgaagcaggt | gctgggaaac | 360 |
| aagcctgaaa | actactctga | tgcgaaatcc | gatttggacg | cccattcaga | tacctacttc | 420 |
| aacacgcatc | accctctcc | cgagcaaaga | cctaggatta | tattattccc | tcatactacc | 480 |
| gaagaagttt | ccaaaatttt | gaaaatatgt | cacgataaca | acatgccagt | tgtacccttc | 540 |
| tcgggcggaa | cgtccttgga | ggggcacttc | ctgcctacaa | gaattggaga | taccataacc | 600 |
| gtagacctgt | ccaagtttat | gaataacgtc | gtaaaatttg | acaagctgga | cctggacatc | 660 |
| accgtgcagg | ccggtctacc | ctgggaggat | ttgaatgact | atttgagcga | ccacggtttg | 720 |
| atgtttggct | gtgaccctgg | tccaggtgca | cagattggtg | gttgcattgc | taattcttgt | 780 |
| tcaggaacca | acgcctaccg | ttacggtacc | atgaaggaga | atattataaa | catgactata | 840 |
| gtgttgccgg | acgggaccat | tgtcaagacg | aagaaaagac | ccagaaagtc | gagcgctggc | 900 |
| tataacttaa | atggtttatt | tgtgggaagt | gaaggtaccc | taggtattgt | tactgaagct | 960 |
| actgtcaagt | gtcatgtcaa | gcccaaagct | gaaactgttg | cggtggtatc | ctttgatact | 1020 |
| atcaaggatg | cggccgcatg | tgcttctaat | ctgactcaga | gtggtattca | tttgaacgcc | 1080 |
| atggagttac | tggatgaaaa | tatgatgaag | ttgatcaacg | catctgaatc | cacggacaga | 1140 |
| tgtgattggg | tagagaaacc | aactatgttt | ttcaagattg | gtgggagatc | tcccaacatt | 1200 |
| gtcaatgctc | ttgtggatga | agttaaggct | gtcgcccagt | taaatcactg | caacagtttt | 1260 |
| cagtttgcta | agatgatga | cgaaaaattg | gaattatggg | aagctagaaa | ggtcgcgcta | 1320 |
| tggtctgtgc | tagacgctga | taagagcaaa | gacaaatcag | ctaaaatttg | gacaactgat | 1380 |
| gtagctgttc | ctgtgtcgca | gttcgacaag | gttattcacg | aaactaaaaa | ggacatgcaa | 1440 |
| gctagtaagc | tgatcaacgc | cattgttggt | catgcaggtg | atggtaactt | ccatgcattc | 1500 |
| atcgtctaca | gaaccctga | agaacacgaa | acctgtagcc | aacttgttga | cagaatggtc | 1560 |
| aagagagcac | tgaacgcaga | aggcacttgc | acgggtgaac | acggtgttgg | tattggtaaa | 1620 |
| agagagtact | gctcgaaga | attaggtgaa | gcacccgtcg | atttgatgag | aaagattaag | 1680 |
| ctagctattg | acccaaagag | aatcatgaac | ccggacaaaa | tctttaaaac | tgatccaaac | 1740 | gagcccgcta atgattacag gtga                                          1764

<210> SEQ ID NO 13
<211> LENGTH: 332
<212> TYPE: PRT
<213> ORGANISM: Bos Taurus

<400> SEQUENCE: 13

Met Ala Thr Leu Lys Asp Gln Leu Ile Gln Asn Leu Leu Lys Glu Glu
1               5                   10                  15

His Val Pro Gln Asn Lys Ile Thr Ile Val Gly Val Gly Ala Val Gly
            20                  25                  30

Met Ala Cys Ala Ile Ser Ile Leu Met Lys Asp Leu Ala Asp Glu Val
        35                  40                  45

Ala Leu Val Asp Val Met Glu Asp Lys Leu Lys Gly Glu Met Met Asp
    50                  55                  60

Leu Gln His Gly Ser Leu Phe Leu Arg Thr Pro Lys Ile Val Ser Gly
65                  70                  75                  80

Lys Asp Tyr Asn Val Thr Ala Asn Ser Arg Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Ile Val Lys Tyr Ser
        115                 120                 125

Pro Asn Cys Lys Leu Leu Val Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Ile Leu Gly Glu
            180                 185                 190

His Gly Asp Ser Ser Val Pro Val Trp Ser Gly Val Asn Val Ala Gly
        195                 200                 205

Val Ser Leu Lys Asn Leu His Pro Glu Leu Gly Thr Asp Ala Asp Lys
    210                 215                 220

Glu Gln Trp Lys Ala Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
        275                 280                 285

Leu Ser Val Pro Cys Ile Leu Gly Gln Asn Gly Ile Ser Asp Val Val
    290                 295                 300

Lys Val Thr Leu Thr His Glu Glu Ala Cys Leu Lys Lys Ser Ala
305                 310                 315                 320

Asp Thr Leu Trp Gly Ile Gln Lys Glu Leu Gln Phe
                325                 330

<210> SEQ ID NO 14
<211> LENGTH: 332
<212> TYPE: PRT
<213> ORGANISM: Pelodiscus sinensis japonicus

<400> SEQUENCE: 14

```
Met Ser Val Lys Glu Leu Leu Ile Gln Asn Val His Lys Glu His
 1               5                  10                  15

Ser His Ala His Asn Lys Ile Thr Val Val Gly Val Gly Ala Val Gly
             20                  25                  30

Met Ala Cys Ala Ile Ser Ile Leu Met Lys Asp Leu Ala Asp Glu Leu
         35                  40                  45

Ala Leu Val Asp Val Ile Glu Asp Lys Leu Arg Gly Glu Met Leu Asp
     50                  55                  60

Leu Gln His Gly Ser Leu Phe Leu Arg Thr Pro Lys Ile Val Ser Gly
 65                  70                  75                  80

Lys Asp Tyr Ser Val Thr Ala His Ser Lys Leu Val Ile Ile Thr Ala
                 85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Asp Cys Met Leu Leu Val Val Ser Asn Pro Val Asp Ile Leu Thr
    130                 135                 140

Tyr Val Ala Trp Lys Ile Ser Gly Phe Pro Lys His Arg Val Ile Gly
145                 150                 155                 160

Ser Gly Cys Asn Leu Asp Ser Ala Arg Phe Arg Tyr Leu Met Gly Glu
                165                 170                 175

Lys Leu Gly Ile His Ser Leu Ser Cys His Gly Trp Ile Ile Gly Glu
            180                 185                 190

His Gly Asp Ser Ser Val Pro Val Trp Ser Gly Val Asn Val Ala Gly
        195                 200                 205

Val Ser Leu Lys Ala Leu Tyr Pro Asp Leu Gly Thr Asp Ala Asp Lys
    210                 215                 220

Glu His Trp Lys Glu Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Thr Val Met Lys Asn Leu Arg Arg Val His Pro
            260                 265                 270

Ile Ser Thr Met Val Lys Gly Met Tyr Gly Val Ser Ser Asp Val Phe
        275                 280                 285

Leu Ser Val Pro Cys Val Leu Gly Tyr Ala Gly Ile Thr Asp Val Val
    290                 295                 300

Lys Met Thr Leu Lys Ser Glu Glu Glu Lys Leu Arg Lys Ser Ala
305                 310                 315                 320

Asp Thr Leu Trp Gly Ile Gln Lys Glu Leu Gln Phe
                325                 330

<210> SEQ ID NO 15
<211> LENGTH: 332
<212> TYPE: PRT
<213> ORGANISM: Ornithorhynchus anatinus

<400> SEQUENCE: 15

Met Ala Gly Val Lys Glu Gln Leu Ile Gln Asn Leu Leu Lys Glu Glu
 1               5                  10                  15

Tyr Ala Pro Gln Asn Lys Ile Thr Val Val Gly Val Gly Ala Val Gly
             20                  25                  30
```

```
Met Ala Cys Ala Ile Ser Ile Leu Met Lys Asp Leu Ala Asp Glu Leu
             35                  40                  45

Ala Leu Val Asp Val Ile Glu Asp Lys Leu Lys Gly Glu Met Met Asp
 50                  55                  60

Leu Gln His Gly Ser Leu Phe Leu Arg Thr Pro Lys Ile Val Ser Gly
 65                  70                  75                  80

Lys Asp Tyr Ser Val Thr Ala Asn Ser Lys Leu Val Ile Ile Thr Ala
                 85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
                115                 120                 125

Pro Asn Cys Lys Leu Leu Val Val Ser Asn Pro Val Asp Ile Leu Thr
            130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Ile His Ser Thr Ser Cys His Gly Trp Val Ile Gly Glu
            180                 185                 190

His Gly Asp Ser Ser Val Pro Val Trp Ser Gly Val Asn Val Ala Gly
                195                 200                 205

Val Ser Leu Lys Asn Leu His Pro Asp Leu Gly Thr Asp Ala Asp Lys
            210                 215                 220

Glu Gln Trp Lys Asp Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Val Lys Asn Leu Arg Arg Val His Pro
            260                 265                 270

Ile Ser Thr Met Ile Lys Gly Leu Tyr Gly Ile Lys Asp Glu Val Phe
            275                 280                 285

Leu Ser Val Pro Cys Val Leu Gly Gln Asn Gly Ile Ser Asp Val Val
            290                 295                 300

Lys Ile Thr Leu Lys Ser Glu Glu Glu Ala His Leu Lys Lys Ser Ala
305                 310                 315                 320

Asp Thr Leu Trp Gly Ile Gln Lys Glu Leu Gln Phe
                325                 330

<210> SEQ ID NO 16
<211> LENGTH: 332
<212> TYPE: PRT
<213> ORGANISM: Tursiops truncatus

<400> SEQUENCE: 16

Met Ala Thr Val Lys Asp Gln Leu Ile Gln Asn Leu Leu Lys Glu Glu
 1               5                  10                  15

His Val Pro Gln Asn Lys Ile Thr Val Val Gly Val Gly Ala Val Gly
             20                  25                  30

Met Ala Cys Ala Ile Ser Ile Leu Met Lys Asp Leu Ala Asp Glu Leu
             35                  40                  45

Ala Leu Val Asp Val Ile Glu Asp Lys Leu Lys Gly Glu Met Met Asp
 50                  55                  60

Leu Gln His Gly Ser Leu Phe Leu Arg Thr Pro Lys Ile Val Ser Gly
```

```
              65                  70                  75                  80
Lys Asp Tyr Ser Val Thr Ala Asn Ser Lys Leu Val Ile Ile Thr Ala
                    85                  90                  95

Gly Ala Arg Gln Gln Glu Gly Glu Ser Arg Leu Asn Leu Val Gln Arg
                100                 105                 110

Asn Val Asn Ile Phe Lys Phe Ile Val Pro Asn Ile Val Lys Tyr Ser
                115                 120                 125

Pro His Cys Lys Leu Leu Val Val Ser Asn Pro Val Asp Ile Leu Thr
            130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Ile Leu Gly Glu
                180                 185                 190

His Gly Asp Ser Ser Val Pro Val Trp Ser Gly Val Asn Val Ala Gly
            195                 200                 205

Val Ser Leu Lys Asn Leu His Pro Glu Leu Gly Thr Asp Ala Asp Lys
    210                 215                 220

Glu His Trp Lys Ala Ile His Lys Gln Val Val Asp Ser Ala Tyr Glu
225                 230                 235                 240

Val Ile Lys Leu Lys Gly Tyr Thr Ser Trp Ala Val Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
        275                 280                 285

Leu Ser Val Pro Cys Ile Leu Gly Gln Asn Gly Ile Ser Asp Val Val
            290                 295                 300

Lys Val Thr Leu Thr Pro Glu Glu Gln Ala Cys Leu Lys Lys Ser Ala
305                 310                 315                 320

Asp Thr Leu Trp Gly Ile Gln Lys Glu Leu Gln Phe
                325                 330

<210> SEQ ID NO 17
<211> LENGTH: 332
<212> TYPE: PRT
<213> ORGANISM: Rattus norvegicus

<400> SEQUENCE: 17

Met Ala Ala Leu Lys Asp Gln Leu Ile Val Asn Leu Leu Lys Glu Glu
1               5                   10                  15

Gln Val Pro Gln Asn Lys Ile Thr Val Val Gly Val Gly Ala Val Gly
                20                  25                  30

Met Ala Cys Ala Ile Ser Ile Leu Met Lys Asp Leu Ala Asp Glu Leu
            35                  40                  45

Ala Leu Val Asp Val Ile Glu Asp Lys Leu Lys Gly Glu Met Met Asp
    50                  55                  60

Leu Gln His Gly Ser Leu Phe Leu Lys Thr Pro Lys Ile Val Ser Ser
65                  70                  75                  80

Lys Asp Tyr Ser Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
                100                 105                 110
```

```
Asn Val Asn Ile Phe Lys Phe Ile Ile Pro Asn Val Lys Tyr Ser
            115                 120                 125
Pro Gln Cys Lys Leu Leu Ile Val Ser Asn Pro Val Asp Ile Leu Thr
        130                 135                 140
Tyr Val Ala Trp Lys Ile Ser Gly Phe Pro Lys Asn Arg Val Ile Gly
145                 150                 155                 160
Ser Gly Cys Asn Leu Asp Ser Ala Arg Phe Arg Tyr Leu Met Gly Glu
                165                 170                 175
Arg Leu Gly Val His Pro Leu Ser Cys His Gly Trp Val Leu Gly Glu
            180                 185                 190
His Gly Asp Ser Ser Val Pro Val Trp Ser Gly Val Asn Val Ala Gly
        195                 200                 205
Val Ser Leu Lys Ser Leu Asn Pro Gln Leu Gly Thr Asp Ala Asp Lys
    210                 215                 220
Glu Gln Trp Lys Asp Val His Lys Gln Val Val Asp Ser Ala Tyr Glu
225                 230                 235                 240
Val Ile Lys Leu Lys Gly Tyr Thr Ser Trp Ala Ile Gly Leu Ser Val
                245                 250                 255
Ala Asp Leu Ala Glu Ser Ile Met Lys Asn Leu Arg Arg Val His Pro
            260                 265                 270
Ile Ser Thr Met Ile Lys Gly Leu Tyr Gly Ile Lys Glu Asp Val Phe
        275                 280                 285
Leu Ser Val Pro Cys Ile Leu Gly Gln Asn Gly Ile Ser Asp Val Val
    290                 295                 300
Lys Val Thr Leu Thr Pro Asp Glu Glu Ala Arg Leu Lys Lys Ser Ala
305                 310                 315                 320
Asp Thr Leu Trp Gly Ile Gln Lys Glu Leu Gln Phe
                325                 330

<210> SEQ ID NO 18
<211> LENGTH: 999
<212> TYPE: DNA
<213> ORGANISM: Bos Taurus

<400> SEQUENCE: 18
atggcaacat taaaagatca actaatccag aatttgttga agaggagca tgttccacaa      60 aacaaaatca caatcgtcgg cgtaggtgca gtaggtatgg cttgtgccat atccatcttg     120
atgaaagact tagctgatga ggtcgcgctg gttgatgtaa tggaggacaa acttaaagga     180
gaaatgatgg atcttcaaca tggttcactc tttttgagaa ctcctaaaat tgtatccggg     240
aaagattata acgttaccgc caattctaga cttgttataa tcacggctgg tgcaagacaa     300
caggaaggcg aatcaagact taacttagtt cagagaaacg taaacatttt caagtttatc     360
atcccaaata ttgtaaaata ctccccaaat tgcaagttgc tggttgtttc aaatcctgtt     420
gacatattga cttacgttgc cttggaagatt tcaggtttcc caaagaatag agtaatcgga     480
tctggttgca atctcgattc tgctcgtttt aggtatctga gggtgaaag attaggggtt     540 catccattga gttgtcacgg atggattcta ggtgaacatg gagatagttc tgtgcctgtt     600
tggtcaggtg tcaacgtagc aggtgtctct ttgaaaaatc tacacccaga actaggaaca     660
gatgccgaca aggaacaatg gaaggccgtc cacaaacaag tggtggattc tgcctacgaa     720
gtcatcaaat tgaagggcta cacatcttgg gcaattggct tatccgtcgc tgatctggct     780
gaatcaataa tgaaaaacct ccgtagagtg catcctataa gtactatgat taagggttta     840
tacgggatca aggaagatgt ttttctatct gtgccatgta ttttgggcca aaatggaatt     900
```

```
tctgacgttg ttaaagtgac acttactcat gaagaggaag cgtgtttgaa aaagagcgca    960
gacaccttat ggggcatcca aaaggaatta caattctaa                           999
```

<210> SEQ ID NO 19
<211> LENGTH: 348
<212> TYPE: PRT
<213> ORGANISM: Saccharomyces cerevisiae

<400> SEQUENCE: 19

```
Met Ser Ile Pro Glu Thr Gln Lys Gly Val Ile Phe Tyr Glu Ser His
  1               5                  10                  15

Gly Lys Leu Glu Tyr Lys Asp Ile Pro Val Pro Lys Pro Lys Ala Asn
             20                  25                  30

Glu Leu Leu Ile Asn Val Lys Tyr Ser Gly Val Cys His Thr Asp Leu
         35                  40                  45

His Ala Trp His Gly Asp Trp Pro Leu Pro Val Lys Leu Pro Leu Val
     50                  55                  60

Gly Gly His Glu Gly Ala Gly Val Val Val Gly Met Gly Glu Asn Val
 65                  70                  75                  80

Lys Gly Trp Lys Ile Gly Asp Tyr Ala Gly Ile Lys Trp Leu Asn Gly
                 85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Gln
        115                 120                 125

Tyr Ala Thr Ala Asp Ala Val Gln Ala Ala His Ile Pro Gln Gly Thr
    130                 135                 140

Asp Leu Ala Gln Val Ala Pro Ile Leu Cys Ala Gly Ile Thr Val Tyr
145                 150                 155                 160

Lys Ala Leu Lys Ser Ala Asn Leu Met Ala Gly His Trp Val Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Glu Gly Lys Glu
        195                 200                 205

Glu Leu Phe Arg Ser Ile Gly Gly Glu Val Phe Ile Asp Phe Thr Lys
    210                 215                 220

Glu Lys Asp Ile Val Gly Ala Val Leu Lys Ala Thr Asp Gly Gly Ala
225                 230                 235                 240

His Gly Val Ile Asn Val Ser Val Ser Glu Ala Ala Ile Glu Ala Ser
                245                 250                 255

Thr Arg Tyr Val Arg Ala Asn Gly Thr Thr Val Leu Val Gly Met Pro
            260                 265                 270

Ala Gly Ala Lys Cys Cys Ser Asp Val Phe Asn Gln Val Val Lys Ser
        275                 280                 285

Ile Ser Ile Val Gly Ser Tyr Val Gly Asn Arg Ala Asp Thr Arg Glu
    290                 295                 300

Ala Leu Asp Phe Phe Ala Arg Gly Leu Val Lys Ser Pro Ile Lys Val
305                 310                 315                 320

Val Gly Leu Ser Thr Leu Pro Glu Ile Tyr Glu Lys Met Glu Lys Gly
                325                 330                 335

Gln Ile Val Gly Arg Tyr Val Val Asp Thr Ser Lys
            340                 345
```

<210> SEQ ID NO 20
<211> LENGTH: 1047
<212> TYPE: DNA
<213> ORGANISM: Saccharomyces cerevisiae

<400> SEQUENCE: 20

| | | | | | | |
|---|---|---|---|---|---|---|
| atgtctatcc | cagaaactca | aaaggtgtt | atcttctacg | aatcccacgg | taagttggaa | 60 |
| tacaaagata | ttccagttcc | aaagccaaag | gccaacgaat | tgttgatcaa | cgttaaatac | 120 |
| tctggtgtct | gtcacactga | cttgcacgct | tggcacggtg | actggccatt | gccagttaag | 180 |
| ctaccattag | tcggtggtca | cgaaggtgcc | ggtgtcgttg | tcggcatggg | tgaaaacgtt | 240 |
| aagggctgga | agatcggtga | ctacgccggt | atcaaatggt | tgaacggttc | ttgtatggcc | 300 |
| tgtgaatact | gtgaattggg | taacgaatcc | aactgtcctc | acgctgactt | gtctggttac | 360 |
| acccacgacg | ttctttcca | acaatacgct | accgctgacg | ctgttcaagc | cgctcacatt | 420 |
| cctcaaggta | ccgacttggc | ccaagtcgcc | cccatcttgt | gtgctggtat | caccgtctac | 480 |
| aaggctttga | gtctgctaa | cttgatggcc | ggtcactggg | ttgctatctc | cggtgctgct | 540 |
| ggtggtctag | ttctttggc | tgttcaatac | gccaaggcta | tgggttacag | agtcttgggt | 600 |
| attgacggtg | gtgaaggtaa | ggaagaatta | ttcagatcca | tcggtggtga | agtcttcatt | 660 |
| gacttcacta | ggaaaagga | cattgtcggt | gctgttctaa | aggccactga | cggtggtgct | 720 |
| cacggtgtca | tcaacgtttc | cgtttccgaa | gccgctattg | aagcttctac | cagatacgtt | 780 |
| agagctaacg | gtaccaccgt | tttggtcggt | atgccagctg | gtgccaagtg | ttgttctgat | 840 |
| gtcttcaacc | aagtcgtcaa | gtccatctct | attgttggtt | cttacgtcgg | taacagagct | 900 |
| gacaccagag | aagctttgga | cttcttcgcc | agaggtttgg | tcaagtctcc | aatcaaggtt | 960 |
| gtcggcttgt | ctaccttgcc | agaaatttac | gaaaagatgg | aaaagggtca | aatcgttggt | 1020 |
| agatacgttg | ttgacacttc | taaataa | | | | 1047 |

<210> SEQ ID NO 21
<211> LENGTH: 292
<212> TYPE: DNA
<213> ORGANISM: Artificial Sequence
<220> FEATURE:
<223> OTHER INFORMATION: Synthetic CCW12 promoter

<400> SEQUENCE: 21

| | | | | | | |
|---|---|---|---|---|---|---|
| ttcgcggcca | cctacgccgc | tatctttgca | acaactatct | gcgataactc | agcaaatttt | 60 |
| gcatattcgt | gttgcagtat | tgcgataatg | ggagtcttac | ttccaacata | acggcagaaa | 120 |
| gaaatgtgag | aaaattttgc | atcctttgcc | tccgttcaag | tatataaagt | cggcatgctt | 180 |
| gataatcttt | ctttccatcc | tacattgttc | taattattct | tattctcctt | tattctttcc | 240 |
| taacatacca | agaaattaat | cttctgtcat | tcgcttaaac | actatatcaa | ta | 292 |

<210> SEQ ID NO 22
<211> LENGTH: 655
<212> TYPE: DNA
<213> ORGANISM: Artificial Sequence
<220> FEATURE:
<223> OTHER INFORMATION: Synthetic GPD promoter

<400> SEQUENCE: 22

| | | | | | | |
|---|---|---|---|---|---|---|
| agtttatcat | tatcaatact | cgccatttca | aagaatacgt | aaataattaa | tagtagtgat | 60 |
| tttcctaact | ttatttagtc | aaaaaattag | ccttttaatt | ctgctgtaac | ccgtacatgc | 120 |
| ccaaaatagg | gggcgggtta | cacagaatat | ataacatcgt | aggtgtctgg | gtgaacagtt | 180 |

```
tattcctggc atccactaaa tataatggag cccgcttttt aagctggcat ccagaaaaaa    240
aaagaatccc agcaccaaaa tattgttttc ttcaccaacc atcagttcat aggtccattc    300
tcttagcgca actacagaga acaggggcac aaacaggcaa aaacgggca caacctcaat    360 ggagtgatgc aacctgcctg gagtaaatga tgacacaagg caattgaccc acgcatgtat    420
ctatctcatt ttcttacacc ttctattacc ttctgctctc tctgatttgg aaaaagctga    480 aaaaaaggt tgaaaccagt tccctgaaat tattccccta cttgactaat aagtatataa    540
agacggtagg tattgattgt aattctgtaa atctatttct taaacttctt aaattctact    600
tttatagtta gtctttttt tagttttaaa acaccagaac ttagtttcga cggat          655
```

<210> SEQ ID NO 23
<211> LENGTH: 289
<212> TYPE: DNA
<213> ORGANISM: Artificial Sequence
<220> FEATURE:
<223> OTHER INFORMATION: Synthetic CYC promoter

<400> SEQUENCE: 23

```
atttggcgag cgttggttgg tggatcaagc ccacgcgtag gcaatcctcg agcagatccg    60
ccaggcgtgt atatatagcg tggatggcca ggcaacttta gtgctgacac atacaggcat    120
atatatatgt gtgcgacgac acatgatcat atggcatgca tgtgctctgt atgtatataa    180
aactcttgtt ttcttctttt ctctaaatat tctttcctta tacattagga cctttgcagc    240
ataaattact atacttctat agacacgcaa acacaaatac acacactaa                289
```

<210> SEQ ID NO 24
<211> LENGTH: 401
<212> TYPE: DNA
<213> ORGANISM: Artificial Sequence
<220> FEATURE:
<223> OTHER INFORMATION: Synthetic TEF promoter

<400> SEQUENCE: 24

```
atagcttcaa aatgtttcta ctccttttttt actcttccag attttctcgg actccgcgca    60
tcgccgtacc acttcaaaac acccaagcac agcatactaa atttcccctc tttcttcctc    120
tagggtgtcg ttaattaccc gtactaaagg tttggaaaag aaaaaagaga ccgcctcgtt    180
tctttttctt cgtcgaaaaa ggcaataaaa attttttatca cgtttctttt tcttgaaaat    240 ttttttttg atttttttct ctttcgatga cctcccattg atatttaagt taataaacgg    300
tcttcaattt ctcaagtttc agtttcattt ttcttgttct attacaactt tttttacttc    360
ttgctcatta gaaagaaagc atagcaatct aatctaagtt t                        401
```

<210> SEQ ID NO 25
<211> LENGTH: 1468
<212> TYPE: DNA
<213> ORGANISM: Artificial Sequence
<220> FEATURE:
<223> OTHER INFORMATION: Synthetic ADH promoter

<400> SEQUENCE: 25

```
gccgggatcg aagaaatgat ggtaaatgaa ataggaaatc aaggagcatg aaggcaaaag    60
acaaatataa gggtcgaacg aaaaataaag tgaaagtgt tgatatgatg tatttggctt    120
tgcggcgccg aaaaaacgag tttacgcaat tgcacaatca tgctgactct gtggcggacc    180
cgcgctcttg ccggcccggc gataacgctg ggcgtgaggc tgtgcccggc ggagtttttt    240
```

```
gcgcctgcat tttccaaggt ttaccctgcg ctaaggggcg agattggaga agcaataaga    300
atgccggttg ggggttgcgat gatgacgacc acgacaactg gtgtcattat ttaagttgcc    360
gaaagaacct gagtgcattt gcaacatgag tatactagaa gaatgagcca agacttgcga    420
gacgcgagtt tgccggtggt gcgaacaata gagcgaccat gaccttgaag gtgagacgcg    480
cataaccgct agagtacttt gaagaggaaa cagcaatagg gttgctacca gtataaatag    540
acaggtacat acaacactgg aaatggttgt ctgtttgagt acgctttcaa ttcatttggg    600
tgtgcacttt attatgttac aatatggaag ggaactttac acttctccta tgcacatata    660
ttaattaaag tccaatgcta gtagagaagg ggggtaacac ccctccgcgc tcttttccga    720
tttttttcta aaccgtggaa tatttcggat atcctttgt tgtttccggg tgtacaatat    780
ggacttcctc ttttctggca accaaaccca tacatcggga ttcctataat accttcgttg    840
gtctccctaa catgtaggtg gcggagggga gatatacaat agaacagata ccagacaaga    900
cataatgggc taaacaagac tacaccaatt acactgcctc attgatggtg gtacataacg    960
aactaatact gtagccctag acttgatagc catcatcata tcgaagtttc actacccttt   1020
ttccatttgc catctattga agtaataata ggcgcatgca acttcttttc tttttttttc   1080
ttttctctct cccccgttgt tgtctcacca tatccgcaat gacaaaaaaa tgatggaaga   1140
cactaaagga aaaattaac gacaaagaca gcaccaacag atgtcgttgt tccagagctg    1200
atgaggggta tctcgaagca cacgaaactt tttccttcct tcattcacgc acactactct   1260
ctaatgagca acggtatacg gccttccttc cagttacttg aatttgaaat aaaaaaaagt   1320
ttgctgtctt gctatcaagt ataaatagac ctgcaattat taatcttttg tttcctcgtc   1380
attgttctcg ttcccttttct tccttgtttc tttttctgca caatatttca agctatacca   1440
agcatacaat caactccaag ctggccgc                                      1468
```

<210> SEQ ID NO 26
<211> LENGTH: 252
<212> TYPE: DNA
<213> ORGANISM: Artificial Sequence
<220> FEATURE:
<223> OTHER INFORMATION: Synthetic CYC1 terminator

<400> SEQUENCE: 26

```
tcatgtaatt agttatgtca cgcttacatt cacgccctcc ccccacatcc gctctaaccg     60
aaaaggaagg agttagacaa cctgaagtct aggtccctat ttatttttttt atagttatgt   120 tagtattaag aacgttattt atatttcaaa tttttctttt ttttctgtac agacgcgtgt   180
acgcatgtaa cattatactg aaaaccttgc ttgagaaggt tttgggacgc tcgaaggctt   240
taatttgcgg cc                                                       252
```

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27

```
ttgcataata ttgtccgctg                                                20
```

<210> SEQ ID NO 28
<211> LENGTH: 61
<212> TYPE: DNA
<213> ORGANISM: Artificial Sequence

```
<220> FEATURE:
<223> OTHER INFORMATION: primer

<400> SEQUENCE: 28
ccaattcgcc ctatagtgag tcgtattaca gggaacaaac ccaaatctga ttccaaggag      60
a                                                                     61

<210> SEQ ID NO 29
<211> LENGTH: 57
<212> TYPE: DNA
<213> ORGANISM: Artificial Sequence
<220> FEATURE:
<223> OTHER INFORMATION: primer

<400> SEQUENCE: 29
agcttttgtt ccctttagtg agggttaatt ctgttgaatt ggcttaagtc tgggtcc         57

<210> SEQ ID NO 30
<211> LENGTH: 22
<212> TYPE: DNA
<213> ORGANISM: Artificial Sequence
<220> FEATURE:
<223> OTHER INFORMATION: primer

<400> SEQUENCE: 30
gtgtctagtc ttctattacg ct                                              22

<210> SEQ ID NO 31
<211> LENGTH: 19
<212> TYPE: DNA
<213> ORGANISM: Artificial Sequence
<220> FEATURE:
<223> OTHER INFORMATION: primer

<400> SEQUENCE: 31
ttgagataag cacactgca                                                  19

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
caacatcacc caattcatcg                                                 20

<210> SEQ ID NO 33
<211> LENGTH: 21
<212> TYPE: DNA
<213> ORGANISM: Artificial Sequence
<220> FEATURE:
<223> OTHER INFORMATION: primer

<400> SEQUENCE: 33
aacaaatcaa acacccacac c                                               21

<210> SEQ ID NO 34
<211> LENGTH: 59
<212> TYPE: DNA
<213> ORGANISM: Artificial Sequence
<220> FEATURE:
<223> OTHER INFORMATION: primer

<400> SEQUENCE: 34
```
ccaattcgcc ctatagtgag tcgtattact ataactacga aactgccaat accaagcca    59

<210> SEQ ID NO 35
<211> LENGTH: 60
<212> TYPE: DNA
<213> ORGANISM: Artificial Sequence
<220> FEATURE:
<223> OTHER INFORMATION: primer

<400> SEQUENCE: 35
agcttttgtt ccctttagtg agggttaatt tcgtttacaa caactaccca atgaagaacc    60

<210> SEQ ID NO 36
<211> LENGTH: 22
<212> TYPE: DNA
<213> ORGANISM: Artificial Sequence
<220> FEATURE:
<223> OTHER INFORMATION: primer

<400> SEQUENCE: 36
aaatacaccc atacatacgg ac    22

<210> SEQ ID NO 37
<211> LENGTH: 19
<212> TYPE: DNA
<213> ORGANISM: Artificial Sequence
<220> FEATURE:
<223> OTHER INFORMATION: primer

<400> SEQUENCE: 37
gtcctcggta gatcaggtc    19

<210> SEQ ID NO 38
<211> LENGTH: 20
<212> TYPE: DNA
<213> ORGANISM: Artificial Sequence
<220> FEATURE:
<223> OTHER INFORMATION: primer

<400> SEQUENCE: 38
aagtacatcc ttgtcgagcc    20

<210> SEQ ID NO 39
<211> LENGTH: 24
<212> TYPE: DNA
<213> ORGANISM: Artificial Sequence
<220> FEATURE:
<223> OTHER INFORMATION: primer

<400> SEQUENCE: 39
tctctataat gaagaccctt gtgc    24

<210> SEQ ID NO 40
<211> LENGTH: 57
<212> TYPE: DNA
<213> ORGANISM: Artificial Sequence
<220> FEATURE:
<223> OTHER INFORMATION: primer

<400> SEQUENCE: 40
ccaattcgcc ctatagtgag tcgtattact atgcgggaac tgtattagcg acatagg    57

<210> SEQ ID NO 41
<211> LENGTH: 60
<212> TYPE: DNA
<213> ORGANISM: Artificial Sequence
<220> FEATURE:
<223> OTHER INFORMATION: primer

<400> SEQUENCE: 41
agcttttgtt ccctttagtg agggttaatt cgacgtgctg tataatgaag tttatgaggg    60

<210> SEQ ID NO 42
<211> LENGTH: 22
<212> TYPE: DNA
<213> ORGANISM: Artificial Sequence
<220> FEATURE:
<223> OTHER INFORMATION: primer

<400> SEQUENCE: 42
gtggatattt acagaacgat gc    22

<210> SEQ ID NO 43
<211> LENGTH: 21
<212> TYPE: DNA
<213> ORGANISM: Artificial Sequence
<220> FEATURE:
<223> OTHER INFORMATION: primer

<400> SEQUENCE: 43
gcacaacacg agatctttca c    21

<210> SEQ ID NO 44
<211> LENGTH: 23
<212> TYPE: DNA
<213> ORGANISM: Artificial Sequence
<220> FEATURE:
<223> OTHER INFORMATION: primer

<400> SEQUENCE: 44
aaagagaaga ggtacaaagg agg    23

<210> SEQ ID NO 45
<211> LENGTH: 19
<212> TYPE: DNA
<213> ORGANISM: Artificial Sequence
<220> FEATURE:
<223> OTHER INFORMATION: primer

<400> SEQUENCE: 45
gtacggctcc tcaactctc    19

<210> SEQ ID NO 46
<211> LENGTH: 55
<212> TYPE: DNA
<213> ORGANISM: Artificial Sequence
<220> FEATURE:
<223> OTHER INFORMATION: primer

<400> SEQUENCE: 46
ccaattcgcc ctatagtgag tcgtattaca cggaagctca agaaatcttt ccagc    55

<210> SEQ ID NO 47
<211> LENGTH: 57
<212> TYPE: DNA
<213> ORGANISM: Artificial Sequence
<220> FEATURE:
<223> OTHER INFORMATION: primer

<400> SEQUENCE: 47
agcttttgtt ccctttagtg agggttaatt gctattgacc caaagagaat catgaac    57

<210> SEQ ID NO 48
<211> LENGTH: 21
<212> TYPE: DNA
<213> ORGANISM: Artificial Sequence
<220> FEATURE:
<223> OTHER INFORMATION: primer

<400> SEQUENCE: 48
tctctgatgc tgccaatagt c                                              21

<210> SEQ ID NO 49
<211> LENGTH: 20
<212> TYPE: DNA
<213> ORGANISM: Artificial Sequence
<220> FEATURE:
<223> OTHER INFORMATION: primer

<400> SEQUENCE: 49
cgtagccata ctaacttggt                                                20

<210> SEQ ID NO 50
<211> LENGTH: 21
<212> TYPE: DNA
<213> ORGANISM: Artificial Sequence
<220> FEATURE:
<223> OTHER INFORMATION: primer

<400> SEQUENCE: 50
tcatcacact ttgaacactg g                                              21

<210> SEQ ID NO 51
<211> LENGTH: 44
<212> TYPE: DNA
<213> ORGANISM: Artificial Sequence
<220> FEATURE:
<223> OTHER INFORMATION: primer

<400> SEQUENCE: 51
ctatagggcg aattggactg taccgaatat ctgtgtccta atga                     44

<210> SEQ ID NO 52
<211> LENGTH: 53
<212> TYPE: DNA
<213> ORGANISM: Artificial Sequence
<220> FEATURE:
<223> OTHER INFORMATION: primer

<400> SEQUENCE: 52
ctcgaggggg ggcccggtac ctattgatat agtgtttaag cgaatgacag aag           53

<210> SEQ ID NO 53
<211> LENGTH: 20
<212> TYPE: DNA
<213> ORGANISM: Artificial Sequence
<220> FEATURE:
<223> OTHER INFORMATION: primer

<400> SEQUENCE: 53
tctcaccata tccgcaatga                                                20

<210> SEQ ID NO 54
<211> LENGTH: 61
<212> TYPE: DNA
<213> ORGANISM: Artificial Sequence
<220> FEATURE:
<223> OTHER INFORMATION: primer

<400> SEQUENCE: 54
ccaattcgcc ctatagtgag tcgtattacc aaggaagaaa gggaacgaga acaatgacga    60
g                                                                   61

<210> SEQ ID NO 55
<211> LENGTH: 60
<212> TYPE: DNA
<213> ORGANISM: Artificial Sequence
<220> FEATURE:
<223> OTHER INFORMATION: primer

<400> SEQUENCE: 55
agcttttgtt ccctttagtg agggttaatt gggtcaaatc gttggtagat acgttgttga    60

<210> SEQ ID NO 56
<211> LENGTH: 22
<212> TYPE: DNA
<213> ORGANISM: Artificial Sequence
<220> FEATURE:
<223> OTHER INFORMATION: primer

<400> SEQUENCE: 56
gtggaagaac gattacaaca gg                                            22

<210> SEQ ID NO 57
<211> LENGTH: 21
<212> TYPE: DNA
<213> ORGANISM: Artificial Sequence
<220> FEATURE:
<223> OTHER INFORMATION: primer

<400> SEQUENCE: 57
gtagccctag acttgatagc c                                             21

<210> SEQ ID NO 58
<211> LENGTH: 23
<212> TYPE: DNA
<213> ORGANISM: Artificial Sequence
<220> FEATURE:
<223> OTHER INFORMATION: primer

<400> SEQUENCE: 58
tgaatgacga tgaagataga gcc                                           23

<210> SEQ ID NO 59
<211> LENGTH: 50
<212> TYPE: DNA
<213> ORGANISM: Artificial Sequence
<220> FEATURE:
<223> OTHER INFORMATION: primer

<400> SEQUENCE: 59
gtttcgacgg attctagaaa acaatgggtt ccgagacaaa acattctgca              50

<210> SEQ ID NO 60
<211> LENGTH: 46
<212> TYPE: DNA
<213> ORGANISM: Artificial Sequence
<220> FEATURE:
<223> OTHER INFORMATION: primer

<400> SEQUENCE: 60
ctaattacat gactcgagtc aaacaaaact aggtttgggt agcgct                  46

```
<210> SEQ ID NO 61
<211> LENGTH: 55
<212> TYPE: DNA
<213> ORGANISM: Artificial Sequence
<220> FEATURE:
<223> OTHER INFORMATION: primer

<400> SEQUENCE: 61
ctatagggcg aattggctag cttatcatta tcaatactcg ccatttcaaa gaata         55

<210> SEQ ID NO 62
<211> LENGTH: 46
<212> TYPE: DNA
<213> ORGANISM: Artificial Sequence
<220> FEATURE:
<223> OTHER INFORMATION: primer

<400> SEQUENCE: 62
taaggataag cagaaccgcg tgacataact aattacatga ctcgag                    46

<210> SEQ ID NO 63
<211> LENGTH: 59
<212> TYPE: DNA
<213> ORGANISM: Artificial Sequence
<220> FEATURE:
<223> OTHER INFORMATION: primer

<400> SEQUENCE: 63
aatcttgtgc tattgcagtc ctcttttata tacagtataa tacgactcac tatagggcg      59

<210> SEQ ID NO 64
<211> LENGTH: 60
<212> TYPE: DNA
<213> ORGANISM: Artificial Sequence
<220> FEATURE:
<223> OTHER INFORMATION: primer

<400> SEQUENCE: 64
atgcgaattg cgtaattcac ggcgataacg tagtattaat taaccctcac taaagggaac    60

<210> SEQ ID NO 65
<211> LENGTH: 19
<212> TYPE: DNA
<213> ORGANISM: Artificial Sequence
<220> FEATURE:
<223> OTHER INFORMATION: primer

<400> SEQUENCE: 65
gcccacaact tatcaagtg                                                  19

<210> SEQ ID NO 66
<211> LENGTH: 19
<212> TYPE: DNA
<213> ORGANISM: Artificial Sequence
<220> FEATURE:
<223> OTHER INFORMATION: primer

<400> SEQUENCE: 66
ttataagaca agcgcaggg                                                  19

<210> SEQ ID NO 67
<211> LENGTH: 5457
<212> TYPE: DNA
<213> ORGANISM: Artificial Sequence
<220> FEATURE:
<223> OTHER INFORMATION: Synthetic pCtB1 vector
```

<400> SEQUENCE: 67

```
ctaaattgta agcgttaata ttttgttaaa attcgcgtta aatttttgtt aaatcagctc      60
attttttaac caataggccg aaatcggcaa aatcccttat aaatcaaaag aatagaccga     120
gatagggttg agtacgcatt taagcataaa cacgcactat gccgttcttc tcatgtatat     180
atatatacag gcaacacgca gatataggtg cgacgtgaac agtgagctgt atgtgcgcag     240
ctcgcgttgc attttcggaa gcgctcgttt tcggaaacgc tttgaagttc ctattccgaa     300
gttcctattc tctagctaga aagtatagga acttcagagc gcttttgaaa accaaaagcg     360
ctctgaagac gcactttcaa aaaccaaaa acgcaccgga ctgtaacgag ctactaaaat     420
attgcgaata ccgcttccac aaacattgct caaaagtatc tctttgctat atatctctgt     480
gctatatccc tatataacct acccatccac ctttcgctcc ttgaacttgc atctaaactc     540
gacctctaca ttttttatgt ttatctctag tattactctt tagacaaaaa aattgtagta     600
agaactattc atagagtgaa tcgaaaacaa tacgaaaatg taaacatttc ctatacgtag     660
tatatagaga caaaatagaa gaaaccgttc ataattttct gaccaatgaa gaatcatcaa     720
cgctatcact ttctgttcac aaagtatgcg caatccacat cggtatagaa tataatcggg     780
gatgccttta tcttgaaaaa atgcacccgc agcttcgcta gtaatcagta aacgcgggaa     840
gtggagtcag gcttttttta tggaagagaa aatagacacc aaagtagcct tcttctaacc     900
ttaacggacc tacagtgcaa aaagttatca agagactgca ttatagagcg cacaaaggag     960
aaaaaaagta atctaagatg ctttgttaga aaaatagcgc tctcgggatg catttttgta    1020
gaacaaaaaa gaagtataga ttcttgttg gtaaaatagc gctctcgcgt tgcatttctg    1080
ttctgtaaaa atgcagctca gattctttgt ttgaaaaatt agcgctctcg cgttgcattt    1140
ttgttttaca aaaatgaagc acagattctt cgttggtaaa atagcgcttt cgcgttgcat    1200
ttctgttctg taaaaatgca gctcagattc tttgtttgaa aaattagcgc tctcgcgttg    1260
catttttgtt ctacaaaatg aagcacagat gcttcgttaa tgtgctgcaa ggcgattaag    1320
ttgggtaacg ccagggtttt cccagtcacg acgttgtaaa acgacggcca gtgaattgta    1380
atacgactca ctatagggcg aattgggtac cgggcccccc ctcgaggtcg acggtatcga    1440
taagcttgat atcgaattcc tgcagcccgg gggatccact agttctagag cggccgccac    1500
cgcggtggag ctcggttctg cttatcctta cgacgtgcct gactacgcct gaacccgatg    1560
caaatgagac gatcgtctat tcctggtccg gttttctctg ccctctcttc tattcacttt    1620
ttttatactt tatataaaat tatataaatg acataactga aacgccacac gtcctctcct    1680
attcgttaac gcctgtctgt agcgctgtta ctgaagctgc gcaagtagtt ttttcaccgt    1740
ataggccctc ttttctctc tctttctttc tctcccgcgc tgatctcttc ttcgaaacac    1800
agagtgcacc ataccacctt ttcaattcat catttttttt ttattctttt ttttgatttc    1860
ggtttccttg aaatttttt gattcggtaa tctccgaaca gaaggaagaa cgaaggaagg    1920
agcacagact tagattggta tatatacgca tatgtagtgt tgaagaaaca tgaaattgcc    1980
cagtattctt aacccaactg cacagaacaa aaacctccag gaaacgaaga taaatcatgt    2040
cgaaagctac atataaggaa cgtgctgcta ctcatcctag tcctgttgct gccaagctat    2100
ttaatatcat gcacgaaaag caaacaaact tgtgtgcttc attggatgtt cgtaccacca    2160
aggaattact ggagtagtt gaagcattag gtcccaaaat tgtttactaa aaacacatg    2220
tggatatctt gactgatttt tccatggagg gcacagttaa gccgctaaag gcattatccg    2280
```

-continued

```
ccaagtacaa tttttactc ttcgaagaca gaaaatttgc tgacattggt aatacagtca      2340
aattgcagta ctctgcgggt gtatacagaa tagcagaatg ggcagacatt acgaatgcac      2400
acggtgtggt gggcccaggt attgttagcg gtttgaagca ggcggcagaa gaagtaacaa      2460
aggaacctag aggccttttg atgttagcag aattgtcatg caagggctcc ctatctactg      2520
gagaatatac taagggtact gttgacattg cgaagagcga caaagatttt gttatcggct      2580
ttattgctca aagagacatg ggtggaagag atgaaggtta cgattggttg attatgacac      2640
ccggtgtggg tttagatgac aagggagacg cattgggtca acagtataga accgtggatg      2700
atgtggtctc tacaggatct gacattatta ttgttggaag aggactattt gcaaagggaa      2760
gggatgctaa ggtagagggt gaacgttaca gaaaagcagg ctgggaagca tatttgagaa      2820
gatgcggcca gcaaaactaa tcatgtaatt agttatgtca cgcttacatt cacgccctcc      2880
ccccacatcc gctctaaccg aaaaggaagg agttagacaa cctgaagtct aggtccctat      2940
ttatttttt atagttatgt tagtattaag aacgttattt atatttcaaa tttttctttt      3000
ttttctgtac agacgcgtgt acgcatgtaa cattatactg aaaaccttgc ttgagaaggt      3060
tttgggacgc tcgaaggctt taatttgcgt ctgtagcgct gttactgaag ctgcgcaagt      3120
agttttttca ccgtataggc cctctttttc tctctctttc tttctctccc gcgctgatct      3180
cttcttcgaa acatcatgaa taaaaagaaa aaggaaatca agaaaaaaaa gccataattt      3240
atcccacatt tttttttatt gtcgctgttc acaccgcata acgaagatat tggctagcta      3300
accagctttt gttccccttta gtgagggtta atttcgagct tggcgtaatc atggtcatag      3360
ctgtttcctg tgtgaaattg ttatccgctc acaattccac acaacatacg agccggaagc      3420
ataaagtgta aagcctgggg tgcctaatga gtgagctaac tcacattaat tgcgttgcgc      3480
tcactgcccg ctttccagtc gggaaacctg tcgtgccagc tgcattaatg aatcggccaa      3540
cgcgcgggga gaggcggttt gcgtattggg cgctcttccg cttcctcgct cactgactcg      3600
ctgcgctcgg tcgttcggct gcggcgagcg gtatcagctc actcaaaggc ggtaatacgg      3660
ttatccacag aatcagggga taacgcagga aagaacatgt gagcaaaagg ccagcaaaag      3720
gccaggaacc gtaaaaaggc cgcgttgctg gcgtttttcc ataggctccg ccccctgac       3780
gagcatcaca aaaatcgacg ctcaagtcag aggtggcgaa acccgacagg actataaaga      3840
taccaggcgt ttccccctgg aagctccctc gtgcgctctc ctgttccgac cctgccgctt      3900
accggatacc tgtccgcctt tctcccttcg ggaagcgtgg cgctttctca tagctcacgc      3960
tgtaggtatc tcagttcggt gtaggtcgtt cgctccaagc tgggctgtgt gcacgaaccc      4020
cccgttcagc ccgaccgctg cgccttatcc ggtaactatc gtcttgagtc aacccggta       4080
agacacgact tatcgccact ggcagcagcc actggtaaca ggattagcag agcgaggtat      4140
gtaggcggtg ctacagagtt cttgaagtgg tggcctaact acggctacac tagaaggaca      4200
gtatttggta tctgcgctct gctgaagcca gttaccttcg gaaaaagagt ggtagctct       4260
tgatccggca aacaaaccac cgctggtagc ggtggttttt ttgtttgcaa gcagcagatt      4320
acgcgcagaa aaaaggatc tcaagaagat cctttgatct tttctacggg gtctgacgct       4380
cagtggaacg aaaactcacg ttaagggatt ttggtcatga gattatcaaa aaggatcttc      4440
acctagatcc tttaaatta aaatgaagt tttaaatcaa tctaaagtat atatgagtaa       4500
acttggtctg acatcagaag aactcgtcaa gaaggcgata gaaggcgatg cgctgcgaat      4560
cgggagcggc gataccgtaa agcacgagga agcggtcagc ccattcgccg ccaagctctt      4620
cagcaatatc acgggtagcc aacgctatgt cctgatagcg gtccgccaca cccagccggc      4680
```

```
cacagtcgat gaatccagaa aagcggccat tttccaccat gatattcggc aagcaggcat    4740
cgccatgggt cacgacgaga tcctcgccgt cgggcatgct cgccttgagc ctggcgaaca    4800
gttcggctgg cgcgagcccc tgatgctctt cgtccagatc atcctgatcg acaagaccgg    4860
cttccatccg agtacgtgct cgctcgatgc gatgtttcgc ttggtggtcg aatgggcagg    4920
tagccggatc aagcgtatgc agccgccgca ttgcatcagc catgatggat actttctcgg    4980
caggagcaag gtgagatgac aggagatcct gccccggcac ttcgcccaat agcagccagt    5040
cccttcccgc ttcagtgaca acgtcgagca cagctgcgca aggaacgccc gtcgtggcca    5100
gccacgatag ccgcgctgcc tcgtcttgca gttcattcag ggcaccggac aggtcggtct    5160
tgacaaaaag aaccgggcgc ccctgcgctg acagccggaa cacggcggca tcagagcagc    5220
cgattgtctg ttgtgcccag tcatagccga atagcctctc cacccaagcg gccgagaac    5280 ctgcgtgcaa tccatcttgt tcaattcgag tgcattcaac atcagccata ctcttccttt    5340
ttcaatatta ttgaagcatt tatcagggtt attgtctcat gagcggatac atatttgaat    5400
gtatttagaa aaataaacaa atagggggttc cgcgcacatt tccccgaaaa gtgccac     5457
```

GENETICALLY ENGINEERED YEAST CELL WITH ENHANCED EDC ACTIVITY AND CAPABILITY OF PRODUCING LACTATE, METHOD OF PRODUCING THE YEAST CELL, AND METHOD OF PRODUCING LACTATE BY USING THE YEAST CELL

RELATED APPLICATION

This application claims the benefit of Korean Patent Application No. 10-2014-0119374, filed on Sep. 5, 2014, in the Korean Intellectual Property Office, the disclosure of which is incorporated herein in its entirety by reference.

INCORPORATION BY REFERENCE OF ELECTRONICALLY SUBMITTED MATERIALS

Incorporated by reference in its entirety herein is a computer-readable nucleotide/amino acid sequence listing submitted concurrently herewith and identified as follows: One 70,134 Byte ASCII (Text) file named "719359_ST25.TXT-Revised" created on Nov. 11, 2015.

BACKGROUND

1. Field

The present disclosure relates to genetically engineered yeast cells capable of producing lactate, methods of producing the yeast cells, and methods of producing lactate by using the yeast cells.

2. Description of the Related Art

Lactate is an organic acid that is widely used in a variety of industrial fields, including the food, pharmaceutical, chemical, and electronic industries. Lactate is a colorless, odorless, water-soluble, low-volatile material. Lactate is not toxic to the human body, and thus is used as a flavoring agent, a souring agent, a preserving agent, or the like. Lactate is also used as a source of polylactic acid (PLA) that is an environmentally friendly, biodegradable plastic known as an alternate polymeric material. PLA is a polyester-based resin prepared for polymerization by conversion of lactic acid to its dimmer, i.e., lactide, and then, by ring-opening polymerization of the lactide. In this regard, PLA may be processed into a variety of forms, such as films, sheets, fibers, and injections. Accordingly, PLA has been increasingly demanded as a bioplastic material to replace the existing general-purpose petrochemical plastics, such as polyethylene (PE), polypropylene (PP), polyethylene terephthalate (PET), and polystylene (PS). In addition, lactate has both a hydroxyl group and a carboxyl group, and thus has desirable reactivity. Accordingly, lactate is easily converted to industrially important compounds, such as lactate ester, acetaldehyde, or propylene glycol, and thus, in the chemical industry field, PLA also has attracted attention as a next-generation alternative chemical raw material.

In recent years, lactate is industrially produced by a petrochemical synthesis process and a biotechnological fermentation process. According to the petrochemical synthesis process, ethylene derived from crude is oxidized, and via acetaldehyde, lactonitrile is obtained by addition of hydrogen cyanide. Then, lactonitrile is purified by distillation and hydrolyzed by using hydrochloric acid or sulfuric acid, thereby producing lactate. According to the biotechnological fermentation process, renewable carbohydrates, such as starch, sucrose, maltose, glucose, fructose, and xylose, are used as substrates to produce lactate. Thus, in view of the art a strain capable of producing lactate in an effective manner and a method of producing lactate using said strain have been demanded. In order to meet these needs, a method of producing lactate by using a microorganism has been recently developed. However, when using a microorganism, due to its homeostasis, mass production of only one material is restricted, and thus, the present inventive concept is completed in the process of studying solutions for the problem.

SUMMARY

Provided is a genetically engineered yeast cell having increased EDC protein activity compared to the EDC protein activity of a parent cell thereof, wherein the yeast cell produces lactate. Provided is a method of producing a genetically engineered yeast cell that produces lactate, the method comprising overexpressing a polynucleotide that encodes an EDC protein in a yeast cell; and introducing a polynucleotide into the yeast cell that encodes a polypeptide that converts pyruvate to L-lactate.

Provided is a method of producing lactate, the method comprising:

culturing the genetically engineered yeast cell in a cell culture medium, whereby the yeast cell produces lactate.

BRIEF DESCRIPTION OF THE DRAWINGS

These and/or other aspects will become apparent and more readily appreciated from the following description of the exemplary embodiments, taken in conjunction with the accompanying drawings in which:

FIG. 3 is a vector map of a pCS-Ex1 vector.

DETAILED DESCRIPTION

Figure 1:
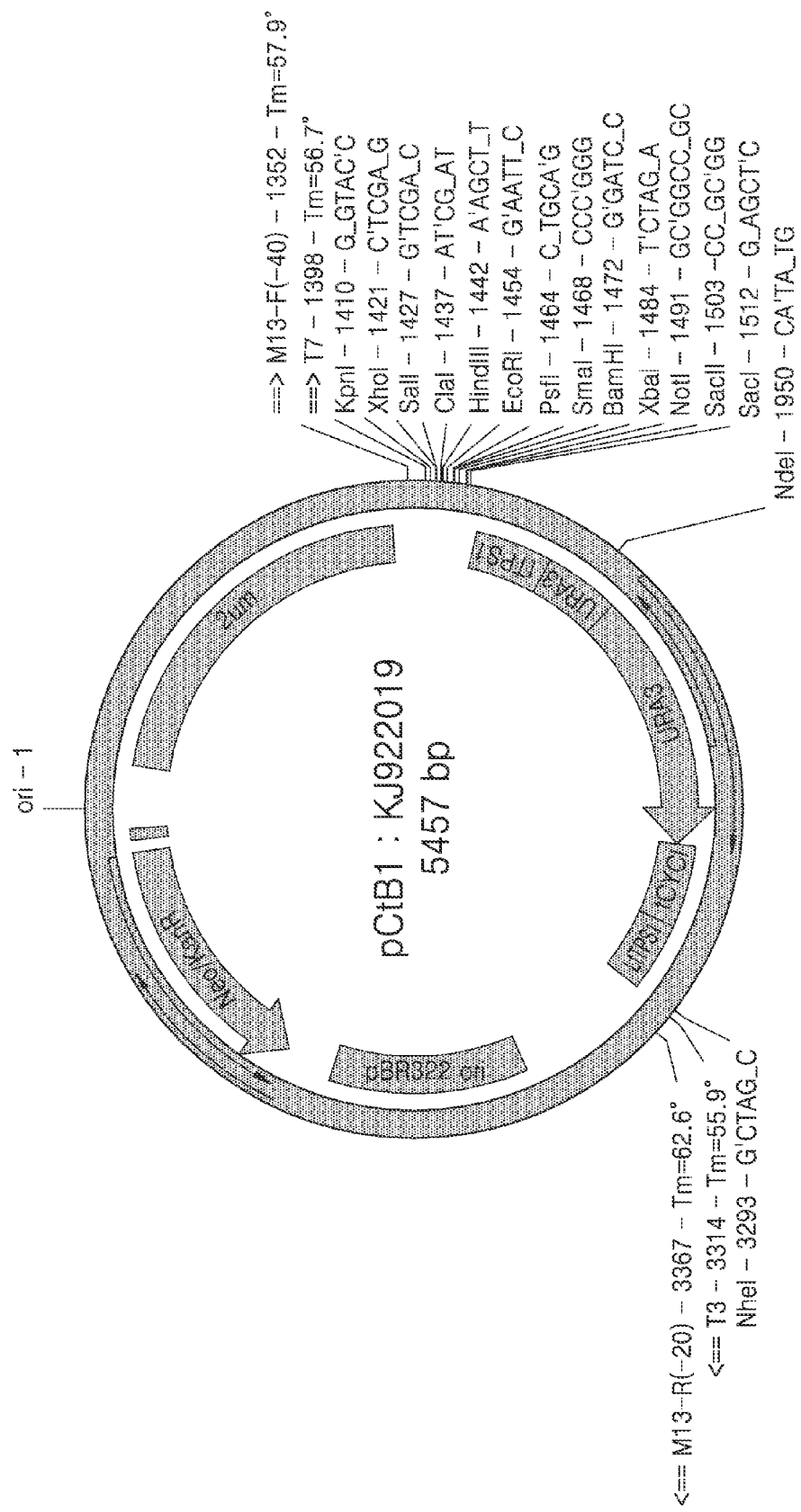
FIG. 1 is a vector map of a pCtB1 vector.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are described below, by referring to the figures, merely to explain and illustrate aspects of the disclosure. As used herein, the term "and/or" includes any and all combinations of one or more of the associated listed items. Expressions such as "at least one of," when preceding a list of elements, modify the entire list of elements and do not modify the individual elements of the list.

The term "genetically engineered" and the like as used herein refers to a biological substance (e.g., cell, polypeptide, nucleic acid, etc.) that contains a non-natural genetic modification, or is produced as the result of a non-natural genetic modification. The non-natural genetic modification can be introduced by any suitable genetic engineering technique.

The terms "increase in activity" or "increased activity" and the like as used herein refers to an detectable increase in a biological activity (e.g., enzyme activity, expression level, etc.) of a cell, polypeptide, or nucleic acid. Increased activity includes, for instance, increases in the amount of a protein or enzyme sufficient to produce a detectable increase in the activity thereof. Increased activity also includes, for instance, increases in the specific activity of a protein or enzyme, which causes a detectable increase in activity even if the amount of protein or enzyme is unchanged. The term "increase in activity" or "increased activity" of a genetically modified (e.g., genetically engineered) cell, protein or enzyme can be any increase as compared to a cell, a protein, or a enzyme of the same type without the genetic modification (e.g., an original, parent, or "wild-type" cell, protein, or enzyme). The term "cell activity" may refer to activity of a specific protein or enzyme in a cell. The activity of a genetically modified or engineered cell, protein, or enzyme may be increased by any amount, for example, about 5% or more, about 10% or more, about 15% or more, about 20% or more, about 30% or more, about 50% or more, about 60% or more, about 70% or more, or about 100% or more enhanced (increased) as compared to the activity of a non-engineered cell, protein, or enzyme, e.g., a wild-type or parent cell, protein, or enzyme, of the same type. Similarly, the activity of a specific protein or enzyme in a cell may be increased by about 5% or more, about 10% or more, about 15% or more, about 20% or more, about 30% or more, about 50% or more, about 60% or more, about 70% or more, or about 100% or more compared to the activity of the same protein or enzyme in a parent cell, e.g., a non-engineered protein or enzyme of the same type in a cell. Cells having enhanced activity of a protein or enzyme may be identified by using any method commonly known in the art.

The term "copy number increase" includes an increase in copy number of a gene (e.g. a polynucleotide) by introduction of a gene into a cell (e.g., the introduction of an endogenous or an exogenous gene into a cell) and/or amplification of an endogenous gene. The introduction of an endogenous gene may be carried out using a vehicle such as a vector. The introduction of a gene into the cell may be a transient introduction, in which the gene is not integrated into the genome, or the introduction of the gene into the cell may result in integration into the genome. The introduction may occur by, for example, introducing a vector containing a polynucleotide that encodes a desired polypeptide into the cell, and replicating the vector in the cell or integrating the polynucleotide into a genome of a cell. The introduction of the vector into the cell may be performed using techniques that are well known to those of ordinary skill in the art, such as heat shock transformation, electroporation, and/or the exposure of the cell to divalent cations.

The polynucleotide having an increased copy number may be endogenous or exogenous. An endogenous gene refers to a gene present in a genetic material within a microorganism prior to a given genetic modification. An exogenous gene refers to a gene that is introduced into a host cell, such as a gene integrated into a genome of a host cell. The gene introduced into a host cell may be homologous or heterologous with respect to the host cell.

The term "heterologous" may denote that a gene is not a native gene, but a foreign gene, whereas "homologous" refers to a gene that is native to the host cell.

The term "gene" as used herein refers to a polynucleotide that is expressed by at least one of transcription and translation. An example of a gene is a nucleic acid fragment capable of being transcribed into mRNA or translated into a protein. A "gene" may or may not include a coding region or a regulatory sequence of a 5'-non coding sequence and a 3'-non coding sequence in addition to the coding region.

The term "cell", "strain", or "microorganism" as used herein may include bacteria, yeast, or fungi to be interchangeably used each other.

The term "decrease in activity" or "decreased activity" as used herein refers to any detectable decrease in a biological activity (e.g., enzyme activity, expression level, etc.) of a cell, polypeptide, or nucleic acid. Decreased activity includes, for instance, decreases in the amount of a protein or enzyme sufficient to produce a detectable increase in the activity thereof. Decreased activity also includes, for instance, decreases in the specific activity of a protein or enzyme, which causes a detectable decrease in activity even if the amount of protein or enzyme is unchanged. A decrease in activity of a genetically modified (genetically engineered) cell, protein, or enzyme can be any decrease as compared to a cell, protein, or enzyme without the genetic modification (e.g., a genetically non-engineered cell, such as a parent or "wild-type" cell, protein, or enzyme). The term "decrease in activity" or "decreased activity" refers to an isolated enzyme or polypeptide that has lower activity than an original or wild-type enzyme or polypeptide. The term "decrease in activity" or "decreased activity" also refers to complete elimination of activity. The activity of a genetically modified cell, protein, or enzyme (e.g., enzymatic activity in conversion of a substrate of a modified (e.g., genetically engineered) cell or enzyme to a product) may be reduced by any amount, such as by about 20% or more, about 30% or more, about 40% or more, about 50% or more, about 55% or more, about 60% or more, about 70% or more, about 75% or more, about 80% or more, about 85% or more, about 90% or more, about 95% or more, or about 100% reduced compared to the activity of a non-engineered cell or enzyme, e.g., a parent or a wild-type cell, protein, or enzyme. The decrease in activity of an enzyme or cell may be identified by using any method commonly known in the art. The decrease in activity may include situations where an enzyme has no activity or reduced activity even when the enzyme is expressed as compared to a cell having a gene that is not modified, e.g., a parent cell or a wild-type cell, or a case where a gene encoding the enzyme is not expressed or an expression amount of the gene is decreased compared to an expression amount of an the enzyme in a non-genetically engineered cell.

The term "parent cell" as used herein may denote an original cell, for example, a non-engineered cell of the same type with respect to an engineered yeast cell. With respect to a particular genetic modification, the "parent cell" can be a cell that lacks the particular genetic modification, but is identical in all other respects. In this regard, the parent cell may be a cell used as a starting material to produce a genetically engineered yeast cell having enhanced activity of a given protein (e.g., a protein having 95% or more sequence identity with an EDC enzyme).

With regard to a subject cell having a particular genetic modification, a parent cell is identical to the subject cell with the exception of the genetic modification, and accordingly, may be a reference cell with respect to the genetically modified cell. The term "genetic modification" refers to an artificially modified configuration or structure of a genetic material (e.g., an exogenous protein, a mutation in a polynucleotide, etc.) of a cell. The parent cell may be a cell without the subject genetic modification, e.g., a cell that is not genetically engineered to have enhanced activity of EDC. The parent cell may be a parent yeast cell.

The term "wild-type" polypeptide or polynucleotide refers to a polypeptide or polynucleotide without specific genetic modification as might be found in nature.

The term "disruption" as used herein may denote a genetic modification (e.g., a mutation, a substitution, or a deletion of one or more nucleotides or a gene) that causes a decrease in the expression of a referenced gene. The term "disruption" may include a case where the referenced gene is genetically engineered to have no expression (hereinafter, referred to as "inactivation" of a gene), or a case where the referenced gene is genetically engineered to be expressed at a reduced expression amount (hereinafter, referred to as "attenuation" of a gene). The inactivation of the gene may include not only situations where a functional product of a gene is not expressed, but also situations where a gene is expressed without the expression of the functional product (e.g., expression of a non-functional gene product). The attenuation of the gene may denote a decrease in expression of a gene, or a decrease in function of the expressed gene product (e.g., expression of a gene product with reduced function). That is, the attenuation of the gene may denote a decrease in the functional product even if the expression of the gene itself is increased. The functional product of the gene may refer to a biochemical activity or physiological function (e.g., enzyme activity) that a product of a gene (e.g., an enzyme) has in a parent cell or a wild-type cell. Therefore, the disruption may include functional disruption of the gene. The genetic modification may include: modification by introduction of a polynucleotide encoding a polypeptide; substitution, addition, insertion, or deletion of at least one nucleotide of a gene (polynucleotide); or chemical mutation of genetic material. The genetic modification may be associated with a coding region or a functional fragment thereof of a heterologous, a homologous, or a heterologous and homologous polypeptide with respect to the referenced species. In addition, the genetic modification may include modification in non-coding regulatory regions to modify expression of a gene or an operon, wherein the non-coding regulatory regions may include a 5'-non coding sequence and/or a 3'-non coding sequence.

The disruption of the gene may occur by genetic engineering methods, such as homologous recombination, directed mutagenesis, or molecular evolution. When a cell includes a plurality of the same genes or two or more paralogs of the gene, one or more genes may be disrupted. For example, the genetic modification may involve transformation in cells using a vector that includes a partial sequence of the gene, followed by the culturing of the cells in a cell culture medium, whereby homologous recombination of the partial sequence occurs with endogenous genes in the cells, so that the genes are disrupted. The cells that have undergone the homologous recombination are selected by using a selection marker, such as an antibiotic resistant gene.

The term "sequence identity" of a polypeptide or polynucleotide as used herein refers to a degree of sameness in an amino acid residue or a base in a specific region of two sequences that are aligned to best match each other for comparison. The sequence identity is a value obtained via alignment and comparison of the two sequences in the specific region for comparison, in which a partial sequence in the specific region for comparison may be added or deleted with respect to a reference sequence. The sequence identity represented in a percentage may be calculated by, for example, comparing two sequences that are aligned to best match each other in the specific region for comparison, determining matched sites with the same amino acid or base in the two sequences to obtain the number of the matched sites, dividing the number of the matched sites in the two sequences by a total number of sites in the compared specific regions (i.e., a size of the compared region), and multiplying a result of the division by 100 to obtain a sequence identity as a percentage. The sequence identity as a percentage may be determined using a known sequence comparison program, for example, BLASTP or BLASTN (NCBI), CLC Main Workbench (CLC bio), or MegAlign™ (DNASTAR Inc).

In identifying a polypeptide or polynucleotide with the same or similar function or activity with respect to various types of species, any various levels of sequence identity may be applied. For example, the sequence identity may be about 50% or more, about 55% or more, about 60% or more, about 65% or more, about 70% or more, about 75% or more, about 80% or more, about 85% or more, about 90% or more, about 95% or more, about 96% or more, about 97% or more, about 98% or more, about 99% or more, or 100%.

The term "exogenous" as used herein denotes introduction of a referenced molecule (e.g., a polynucleotide) or a referenced activity to a host cell. The introduction of a molecule denotes, for example, introduction to a host genetic material of a nucleic acid encoding a protein or an enzyme by insertion of the exogenous nucleic acid into the host chromosomes, or introduction of the nucleic acid into a host cell as a non-chromosomal genetic material such as a plasmid. Regarding the expression of the encoding nucleic acid, the term "exogenous" denotes introduction of the encoding nucleic acid in an expressible form into a cell. In regard to the biosynthesis activity, the term "exogenous" denotes activity introduced to a host parent cell. The source of the exogenous gene may include, for example, homologous or heterologous nucleic acid that encodes a protein or an enzyme that expresses the referenced activity after being introduced to the host parent cell. Thus, the term "endogenous" denotes to a referenced molecule or a referenced activity that is already present in the host cell. Similarly, regarding the expression of the encoding nucleic acid, the term "endogenous" denotes expression of the nucleic acid encoding a protein or enzyme that is already expressed in the cell. The term "heterologous" denotes a molecule or an activity derived from a source other than the referenced species. The term "homologous" denotes a molecule or an activity from the host parent cell. Therefore, the exogenous expression of the nucleic acid encoding a protein or enzyme may include any one of heterologous or homologous encoding nucleic acids, or may include both heterologous and homologous nucleic acids encoding a protein or an enzyme.

The term "lactate" as used herein refers to lactic acid as well as its anion form, a salt thereof, a solvate, a polymorph, or a combination thereof. The salt may be, for example, an inorganic acid salt, an organic acid salt, or a metal salt. The inorganic acid salt may be hydrochloride, bromate, phosphate, sulfate, or disulfate. The organic acid salt may be formate, acetate, propionate, lactate, oxalate, tartrate, malate, maleate, citrate, fumarate, besylate, camsylate, edisylate, trifluoroacetate, benzoate, gluconate, methansulfonate, glycolate, succinate, 4-toluenesulfonate, galacturonate, embonate, glutamate, or aspartate. The metal salt may be a calcium salt, a sodium salt, a magnesium salt, a strontium salt, or a potassium salt.

According to one embodiment, there is provided a genetically engineered yeast cell with the capability of producing lactate and enhanced activity of an EDC protein as compared with activity of an EDC protein in a parent cell of the genetically engineered yeast cell.

The EDC protein may be an mRNA-decapping enhancer protein. The EDC may be an mRNA-binding protein that stimulates the mRNA decapping abilities of DCP1 and DCP2. The EDC may be EDC1 or EDC2. The EDC2 may include an amino acid sequence having about 60% or more, about 70% or more, about 80% or more, about 90% or more, about 95% or more, about 96% or more, about 97% or more, about 98% or more, or about 99% or more sequence identity with an amino acid sequence of SEQ ID NO: 1. For example, the EDC2 may have NCBI reference number of NP 010652.3. A gene encoding the EDC2 may be a polynucleotide having 95% or more sequence identity with respect to an amino acid sequence of SEQ ID NO: 2. The EDC1 may include an amino acid sequence having about 60% or more, about 70% or more, about 80% or more, about 90% or more, about 95% or more, about 96% or more, about 97% or more, about 98% or more, or about 99% or more sequence identity with an amino acid sequence of SEQ ID NO: 3. For example, the EDC1 may have NCBI reference number of NP_011293.1. A gene encoding the EDC1 may be a polynucleotide having 95% or more sequence identity with respect to an amino acid sequence of SEQ ID NO: 4.

The yeast cell may comprise modification in a regulatory sequence affecting gene expression, for example, a modification of the regulatory sequence of the gene encoding the EDC protein. The regulatory sequence affecting gene expression may include a sequence of a promoter for the gene expression or a sequence of a transcription terminator. The regulatory sequence affecting gene expression may include a sequence encoding a motif that influences the gene expression. The motif may include, for example, a secondary structure stability motif, an RNA instability motif, splice activation motif, a polyadenylation motif, an adenine-rich sequence, or an endonuclease recognition site. The sequence of the promoter may be an exogenous promoter that is operably linked to a gene encoding the EDC protein. The promoter may be a constitutive promoter. The promoter may be derived from covalently linked cell wall protein 12 (CCW12), pyruvate deCarboxylase 1 (PDC1), phosphoglycerate kinase (PGK1), transcription enhancer factor-1 (TEF-1), glyceraldehyde-3-phosphate dehydrogenase (TDH1, TDH2, or TDH3), triose phosphate isomerase (TPI1), purine-cytosine permease (PCPL3), or alcohol dehydrogenase (ADH1) genes. In addition, the regulatory sequence in gene expression may include a sequence that improves efficiency of translation. The sequence that improves efficiency of translation may be, for example, a sequence that improves initiation of the translation process, such as a Kozak consensus sequence.

The yeast cell may also have an increase in a copy number of the EDC protein-encoding gene. The yeast cell may include an exogenous gene that encodes the EDC protein. The exogenous gene may be appropriately regulated by an exogenous promoter that is operably linked thereto. The promoter is defined the same as described above.

The yeast cell may belong to *Saccharomyces* genus, *Kluyveromyces* genus, *Candida* genus, *Pichia* genus, *Issatchenkia* genus, *Debaryomyces* genus, *Zygosaccharomyces* genus, *Shizosaccharomyces* genus, or *Saccharomycopsis* genus. *Saccharomyces* genus may be, for example, *S. cerevisiae, S. bayanus, S. boulardii, S. bulderi, S. cariocanus, S. cariocus, S. chevalieri, S. dairenensis, S. ellipsoideus, S. eubayanus, S. exiguus, S. florentinus, S. kluyveri, S. martiniae, S. monacensis, S. norbensis, S. paradoxus, S. pastorianus, S. spencerorum, S. turicensis, S. unisporus, S. uvarum*, or *S. zonatus*.

The yeast cell may have capability of producing L-lactate. The yeast cell may have an activity of a polypeptide that converts pyruvate to L-lactate. The yeast cell may include a gene encoding a polypeptide that converts pyruvate to L-lactate. In the yeast cell, the activity of a polypeptide that converts pyruvate to L-lactate may be increased. The polypeptide that converts pyruvate to L-lactate may be an enzyme that catalyzes the conversion of pyruvate to L-lactate, and for example, the polypeptide may be an L-lactate dehydrogenase (LDH). The LDH may be an NAD(P)-dependent enzyme. In addition, the LDH may be stereo-specific. The NAD(P)-dependent enzyme may be an enzyme that is classified under EC 1.1.1.27 that functions on L-lactate.

In the yeast cell capable of producing lactate, the activity of the LDH may be increased. The yeast cell may include a polynucleotide encoding at least one LDH, and the polynucleotide may be an exogenous gene. The polynucleotide encoding the LDH may be derived from bacteria, yeasts, fungi, mammals, or reptiles. The polynucleotide may be a polynucleotide that encodes at least one LDH selected from the group consisting of *Lactobacillus helveticus, L. bulgaricus, L. johnsonii, L. plantarum, Pelodiscus sinensis japonicus, Ornithorhynchus anatinus, Tursiops truncatus, Rattus norvegicus, Xenopus laevis*, and *Bos taurus*. An LDH derived from *Bos taurus*, an LDH derived from *Pelodiscus sinensis japonicus*, an LDH derived from *Ornithorhynchus anatinus*, an LDH derived from *Tursiops truncatus*, and an LDH derived from *Rattus norvegicus* may each have an amino acid sequence having about 60% or more, about 70% or more, about 80% or more, about 90% or more, about 95% or more, about 96% or more, about 97% or more, about 98% or more, or about 99% or more sequence identity with amino acids of SEQ ID NOS: 13, 14, 15, 16, and 17. For example, a gene encoding the LDH may be a polynucleotide that encodes an amino acid sequence having 95% or more sequence identity with amino acid sequences of SEQ ID NOS: 13, 14, 15, 16, and 17. Alternatively, a gene encoding the LDH may have a polynucleotide sequence of SEQ ID NO: 18.

The gene encoding the LDH may be included in a vector. The vector may include a replication origin, a promoter, an LDH-encoding polynucleotide, and a terminator. The replication origin may include a yeast autonomous replication sequence (ARS). The yeast ARS may be stabilized by a yeast centrometric sequence (CEN). The promoter may be selected from the group consisting of promoters of cytochrome c (CYC), transcription elongation factor (TEF), GPD, ADH, and CCW12 genes. The promoter of the CYC, TEF, GPD, ADH, and CCW12 genes may each include nucleotide sequences of SEQ ID NOS: 23, 24, 22, 25, and 21. The terminator may be selected from the group consisting of terminators of phosphoglycerate kinase 1 (PGK1), cytochrome c 1 (CYC1), galactokinase 1 (GAL1), and trehalose-6-phosphate synthase 1 (TPS1) genes. The terminator of the CYC1 gene may include a nucleotide sequence of SEQ ID NO: 26. The vector may further include a selection marker (e.g., an antibiotic selection marker). A polynucleotide encoding the LDH may be included in a genome at a specific site of the yeast cell. When the polynucleotide encoding the LDH functions on the production of active proteins in a cell, the polynucleotide is considered to be "functional" in a cell.

The yeast cell may include a polynucleotide that encodes one LDH or a polynucleotide that encodes multiple LDH copies, e.g., about 2 to about 10 copies. The yeast cell may include a polynucleotide that encodes multiple LDH copies into, for example, about 1 to about 8, about 1 to about 7, about 1 to about 6, about 1 to about 5, about 1 to about 4, or about 1 to about 3 copies. When the yeast cell includes the polynucleotide encoding multiple LDH copies, each polynucleotide may include copies of the same LDH or copies of at least two different LDHs. The multiple copies of the polynucleotide that encodes exogenous LDHs may be included in the same locus or multiple loci in a genome of a host cell, and the promoter or the terminator of each copy of the polynucleotide may be identical to or different from each other.

In the yeast cell, the activity of one or more pathways that interrupt the production or use of metabolic products involved in lactate production may be reduced. Additionally, the activity of one or more pathways that catalyze or assists in the production or use of metabolic products for producing lactate may be increased.

The yeast cell may additionally comprise a genetic modification such that the activity of a polypeptide that converts pyruvate to acetaldehyde, a polypeptide that converts lactate to pyruvate, a polypeptide that converts dihydroxyacetone phosphate (DHAP) to glycerol-3-phosphate, a polypeptide that converts acetaldehyde to ethanol, aldehyde dehydrogenase, or a combination thereof may be reduced as compared with activity of one or more of these enzymes in a parent cell.

The yeast cell may include a disruption mutation of a gene encoding the polypeptide that converts pyruvate to acetaldehyde. The polypeptide that converts pyruvate to acetaldehyde may be an enzyme that catalyzes the conversion of pyruvate to acetaldehyde and is classified under EC 4.1.1.1. The polypeptide that converts pyruvate to acetaldehyde may be a pyruvate decarboxylase, and for example, may be PDC1. The polypeptide that converts pyruvate to acetaldehyde may include an amino acid sequence having about 60% or more, about 70% or more, about 80% or more, about 90% or more, about 95% or more, about 96% or more, about 97% or more, about 98% or more, or about 99% or more sequence identity with an amino acid sequence of SEQ ID NO: 5. The gene encoding the polypeptide that converts pyruvate to acetaldehyde may include a polynucleotide sequence encoding an amino acid sequence having about 95% or more sequence identity with an amino acid sequence of SEQ ID NO: 5, or may include a polynucleotide sequence of SEQ ID NO: 6. For example, the gene may be PDC1.

The yeast cell may include a disruption mutation of a gene encoding the polypeptide that converts lactate to pyruvate. The polypeptide that converts lactate to pyruvate may be a CYC-dependent enzyme. The polypeptide that converts lactate to pyruvate may be an enzyme that is classified under EC 1.1.2.4 that acts on D-lactate, or that is classified under EC 1.1.2.3 that acts on L-lactate. The polypeptide that converts lactate into pyruvate may be lactate cytochrome c-oxidoreductase, for example, a CYB2 (CAA86721.1), a CYB2A, or a CYB2B. The polypeptide that converts lactate into pyruvate may include an amino acid sequence having about 60% or more, about 70% or more, about 80% or more, about 90% or more, about 95% or more, about 96% or more, about 97% or more, about 98% or more, or about 99% or more sequence identity with an amino acid sequence of SEQ ID NO: 7. The gene encoding the polypeptide that converts lactate into pyruvate may include a polynucleotide sequence encoding an amino acid sequence having about 95% or more sequence identity with an amino acid sequence of SEQ ID NO: 7, or may include a polynucleotide sequence of SEQ ID NO: 8.

The yeast cell may include a disruption mutation of a gene encoding the polypeptide that converts DHAP to glycerol-3-phosphate. The polypeptide that converts DHAP to glycerol-3-phosphate may be a cytosolic glycerol-3-phosphatedehydrogenase, and may be an enzyme that catalyzes reduction of DHAP to glycerol-3-phosphate by using oxidation of NADH or NADP to NAD+ or NADP+. The polypeptide may be an enzyme that is classified under EC 1.1.1.8. The cytosolic glycerol-3-phosphate dehydrogenase may be GPD1. The cytosolic glycerol-3-phosphate dehydrogenase may include an amino acid sequence having about 60% or more, about 70% or more, about 80% or more, about 90% or more, about 95% or more, about 96% or more, about 97% or more, about 98% or more, or about 99% or more sequence identity with an amino acid sequence of SEQ ID NO: 9. The gene encoding the cytosolic glycerol-3-phosphate dehydrogenase may include a polynucleotide sequence encoding an amino acid sequence having a about 95% or more sequence identity with an amino acid sequence of SEQ ID NO: 9, or may include a polynucleotide sequence of SEQ ID NO: 10.

The yeast cell may include a disruption mutation of a gene encoding the polypeptide that converts pyruvate to D-lactate. The polypeptide may be classified under EC. 1.1.2.4. The polypeptide may be D-lactate dehydrogenase (DLD. The DLD may be also called D-lactate ferricytochrome C oxidoreductase. The polypeptide may be DLD1. The polypeptide may include an amino acid sequence having about 60% or more, about 70% or more, about 80% or more, about 90% or more, about 95% or more, about 96% or more, about 97% or more, about 98% or more, or about 99% or more sequence identity with an amino acid sequence of SEQ ID NO: 11. The gene encoding the polypeptide may include a polynucleotide sequence encoding an amino acid sequence having about 95% or more sequence identity with an amino acid sequence of SEQ ID NO: 11. For example, the gene may include a polynucleotide of SEQ ID NO:

In the yeast cell, the yeast cell may include a disruption mutation of a gene encoding the polypeptide that converts acetaldehyde to ethanol. The polypeptide may be an enzyme that catalyzes the conversion of acetaldehyde to ethanol and that is classified under EC. 1.1.1.1. The polypeptide may be an enzyme that catalyzes the conversion of acetaldehyde to ethanol by involving conversion of NADH to NAD+. The polypeptide may be an alcohol dehydrogenase (Adh), and may be Adh1, Adh2, Adh3, Adh4, Adh5, or Adh6. The polypeptide may include an amino acid sequence having about 60% or more, about 70% or more, about 80% or more, about 90% or more, about 95% or more, about 96% or more, about 97% or more, about 98% or more, or about 99% or more sequence identity with an amino acid sequence of SEQ ID NO: 19. The gene encoding the polypeptide may include a polynucleotide sequence encoding an amino acid sequence having about 95% or more of sequence identity with an amino acid sequence of SEQ ID NO: 19, or may include a polynucleotide sequence of SEQ ID NO: 20. For example, the gene may be adh1, adh2, adh3, adh4, adh5, or adh6.

In addition, in the yeast cell according to an exemplary embodiment, the yeast cell may include increased activity of EDC as compared to a parent cell thereof; a disruption mutation of a gene encoding a polypeptide that converts pyruvate to acetaldehyde, a gene encoding a polypeptide that converts lactate to pyruvate, a gene encoding a polypeptide that converts DHAP to glycerol-3-phosphate, a gene encoding a polypeptide that converts pyruvate to D-lactate, a gene encoding a polypeptide that converts acetaldehyde to ethanol, or a combination thereof; and an exogenous gene encoding a polypeptide that converts pyruvate to L-lactate. The yeast cell may be a *S. cerevisiae* yeast cell.

According to another aspect, there is provided a composition for producing lactate, the composition including the yeast cell. The yeast cell is defined the same as described above.

According to another aspect, there is provided a method of producing a yeast cell that produces lactate, the method including: overexpressing a gene that encodes an EDC protein in a yeast cell; and introducing a gene encoding a polypeptide that converts pyruvate to L-lactate.

The method of producing the yeast cell that produces lactate may include a step of overexpressing a gene that encodes an EDC protein in the yeast cell. Here, the terms "yeast cell", "EDC protein", and "gene encoding the EDC protein" are defined the same as described above.

The step of overexpressing the gene encoding the EDC protein may result in overexpression of the EDC protein. That is, the overexpression of the EDC protein may denote that the yeast cell in which the gene encoding the EDC protein is overexpressed is produced in larger amounts or slightly higher steady-state as compared with the EDC protein in the parent cell so that the activity of the EDC protein is high in the yeast cell under the same conditions. In addition, the overexpression of the EDC protein may denote that mRNA encoding the EDC protein is produced in larger amounts or slightly higher steady-state as compared with the EDC protein in the parent cell so that the activity of the EDC protein is high in the yeast cell under the same conditions. Therefore, the overexpression of the EDC protein may be measured by using suitable enzyme analysis to measure an inactive level of the EDC protein in the host cell. The step of overexpressing the gene encoding the EDC protein may comprise introducing a genetic modification into the yeast cell that increases activity of the EDC protein, such as an increase in the copy number of the EDC protein, a modification of a regulatory sequence of a polynucleotide encoding an EDC protein, or a combination thereof.

The method of producing the yeast cell that produces lactate may include a step of introducing a gene encoding a polypeptide that converts pyruvate to L-lactate. In this step, the terms "polypeptide that converts to lactate" and "a gene encoding a polypeptide that converts to lactate" are defined the same as described above. The introduction of the gene may occur by using a vehicle such as a vector. The introduction may be transient introduction, in which the gene is not integrated into the genome, or may be integration of the gene into the genome. The introduction may occur by, for example, introducing a vector that is inserted with a polynucleotide encoding a desired polypeptide into the cell, and then, by replicating the vector in the cell or integrating the polynucleotide into the genome of the cell.

In addition, the method of producing the yeast cell that produces lactate may further include a step of disrupting a gene encoding a polypeptide that converts pyruvate to acetaldehyde, a gene encoding a polypeptide that converts lactate to pyruvate, a gene encoding a polypeptide that converts DHAP to glycerol-3-phosphate, a gene encoding a polypeptide that converts pyruvate to D-lactate, a gene encoding a polypeptide that converts acetaldehyde to ethanol, or a combination thereof. In this step, the terms "polypeptide that converts pyruvate to acetaldehyde", "gene encoding the polypeptide that converts pyruvate to acetaldehyde", "polypeptide that converts lactate to pyruvate", "gene encoding the polypeptide that converts lactate to pyruvate", "polypeptide that converts DHAP to glycerol-3-phosphate", "gene encoding the polypeptide that converts DHAP to glycerol-3-phosphate", "polypeptide that converts pyruvate to D-lactate", "gene encoding the polypeptide converting pyruvate to D-lactate", "polypeptide that converts acetaldehyde to ethanol", "gene encoding the polypeptide converting acetaldehyde to ethanol", and "disruption" are defined the same as described above.

According to another aspect, there is provided a method of producing lactate, the method including culturing the yeast cell in a cell culture medium, whereby the yeast cell produces lactate. The yeast cell is defined the same as described above.

The culturing of the yeast cell may be performed in a medium containing a carbon source, e.g., glucose. The medium used for the culturing of the yeast cell may be any conventional medium suitable for proliferation of the host cell, such as a minimal or complex medium containing appropriate supplements. The suitable medium may be available from a commercial seller or may be manufactured according to known manufacturing methods. The medium for the culturing of the yeast cell may be a medium that satisfies requirements of a particular yeast cell. The medium may be selected from media consisting of carbon sources, nitrogen sources, salts, trace elements, and a combination thereof.

The culture conditions may be appropriately controlled to obtain lactate from the genetically engineered yeast cell. The yeast cell may be cultured in aerotropic conditions. In order to produce lactate, the yeast cell may be cultured in microaerobic or anaerobic conditions. The term "anaerobic conditions" refers to an environment without oxygen. When the term "microaerobic conditions" is used by referring to culture or growth conditions, the microaerobic conditions may include maintaining a dissolved oxygen (DO) concentration of the medium in a range of about 0% to about 10% with respect to a DO concentration of a liquid medium in a saturation state. The microaerobic conditions also include growing or resting cells in a liquid medium or on a solid agar plate placed in a sealed chamber maintained in an atmosphere having oxygen of less than 1%. The concentration of oxygen may be maintained by, for example, sparging the culture in a mixture of $N_2/CO_2$ or in other suitable non-oxygen gases. The oxygen conditions may include a case where the DO concentration is maintained in a range of about 0% to about 10%, for example, about 0% to about 8%, about 0% to about 6%, about 0% to about 4%, or about 0% to about 2%.

The term "culture conditions" may denote conditions required for culturing the yeast cells. The culture conditions may include, for example, a carbon source or a nitrogen source, or oxygen conditions available for the yeast cell. The carbon source available for the yeast cell may include a monosaccharide, a disaccharide, or a polysaccharide, and examples thereof are glucose, fructose, mannose, or galactose. The nitrogen source available for the yeast cell may include an organic nitrogen compound or an inorganic nitrogen compound. Examples of the nitrogen source are amino acids, amides, amines, nitrates, or ammonium salts.

The method of producing lactate may further include collecting lactate from the culture.

The collecting of lactate from the culture may be carried out by using separation methods that are commonly known in the art. The separation methods may include centrifugation, filtration, ion-exchange chromatography, or crystallization. For example, the culture may be centrifuged at a low speed to remove biomass, and then, a supernatant obtained therefrom may be separated through ion-exchange chromatography.

The yeast cell according to an aspect may be used to produce lactate in an effective manner.

The method of producing the yeast cell according to an aspect may be used to produce the yeast cell producing lactate in an effective manner.

The method of producing lactate according to an aspect may be used to produce lactate in an effective manner.

Hereinafter, the present inventive concept will be described in further detail with reference to the following examples. These examples are for illustrative purposes only and are not intended to limit the scope of the present invention.

Example 1: Manufacture of Strain with Capability of Producing L-Lactate

In order to prepare a *S. cerevisiae* CEN.PK2-1 D wild-type strain (MATaura3-52; trp1-289; leu2-3,112; his3Δ1; MAL2-8C; SUC2, EUROSCARF accession number: 30000B) as a strain for producing lactate, gene deletion occurred in main enzymes involved in alcohol fermentation, i.e., a pyruvate decarboxylase (pdc1) gene and an alcohol dehydrogenase (adh1) gene, a main enzyme involved in biosynthesis of glycerol, i.e., a NAD-dependent glycerol-3-phosphate dehydrogenase (gpd1) gene, and proteolytic enzymes of lactate, i.e., an L-lactate cytochrome-c oxidoreductase 2 (cyb2) gene and a D-lactate dehydrogenase (dld1) gene. Then, a lactate dehydrogenase (BtLDH) gene derived from *Bos Taurus* was inserted at the adh1 gene site, thereby manufacturing an MD1304 strain for producing lactate. Each procedure of the strain manufacture is as follows.

1.1: Manufacture of Strain Including pdc1 Deletion

A 260 bp DNA fragment (hereinafter, referred to as 'Fragment 1') was obtained as an amplification product by PCR that was performed by using a genome DNA of the *S. cerevisiae* CEN.PK2-1D wild-type strain as a template and a primer set of SEQ ID NOS: 27 and 28 as primers. A 257 bp DNA fragment (hereinafter, referred to as 'Fragment 2') was obtained as an amplification product by PCR that was performed by using the genome DNA of the *S. cerevisiae* CEN.PK2-1 D wild-type strain as a template and a primer set of SEQ ID NOS: 29 and 30 as primers. A 1,955 bp DNA fragment (hereinafter, referred to as 'Fragment 3') was obtained as an amplification product by PCR that was performed by using a pCtB1 vector (GenBank Accession Number KJ922019) as a template and a primer set of a T7 primer and a T3 primer as primers. FIG. 1 is a view of a pCtB1 vector (GenBank Accession Number KJ922019). Here, the pCtB1 vector had a polynucleotide of SEQ ID NO: 67. These DNA fragments, i.e., Fragments 1, 2, and 3, were combined together, and then, subjected to PCR using a primer set of SEQ ID NOS: 27 and 30 as primers, so as to obtain a 2,414 bp DNA fragment, which is a DNA fragment used to substitute a URA3 terminator BLAST for the PDC1 gene.

Transformation of the DNA fragment occurred in the *S. cerevisiae* CEN.PK2-1 D wild-type strain, and then, strains grown on a minimal medium without containing uracil (SD-URA; Yeast Nitrogen Base 6.7 g, Synthetic Drop-out without uracil 1.92 g, D-glucose 20 g, Bacto Agar 20 g/L) were selected therefrom. Among the selected strains, a strain having identification of a 2,947 bp DNA fragment was obtained by PCR that was performed by using a primer set of SEQ ID NOS: 31 and 32, wherein the primer set had identification of a 2,904 bp DNA fragment from the wild-type strain.

The obtained strain was subjected to a seed culture for one day in an YPD culture medium (Yeast Extract 10 g, Bacto Peptone 20 g, D-glucose 20 g/L). Afterwards, colonies were spread on a 5-FOA culture medium (Yeast Nitrogen Base 6.7 g, Synthetic Drop-out without uracil 1.92 g, uracil 0.1 g, D-glucose 20 g, 5-fluoroorotic acid 1 g, Bacto Agar 20 g/L) to select strains that were grown and developed therefrom. Among the selected strains, PCR was performed again by using a primer set of SEQ ID NOS: 31 and 32, so as to obtain a strain having identification of a 1,553 bp DNA fragment, and that is, a *S. cerevisiae* CEN.PK2-1D (Δpdc1) strain (hereinafter, referred to as 'MD1002 strain') was obtained.

1.2: Manufacture of Strain Including gpd1 Deletion

A 278 bp DNA fragment (hereinafter, referred to as 'Fragment 4') was obtained as an amplification product by PCR that was performed by using the genome DNA of the *S. cerevisiae* CEN.PK2-1 D wild-type strain as a template and a primer set of SEQ ID NOS: 33 and 34 as primers. A 446 bp DNA fragment (hereinafter, referred to as 'Fragment 5') was obtained as an amplification product by PCR that was performed by using the genome DNA of the *S. cerevisiae* CEN.PK2-1 D wild-type strain as a template and a primer set of SEQ ID NOS: 35 and 36 as primers. A 1,955 bp DNA fragment (hereinafter, referred to as 'Fragment 6') was obtained as an amplification product by PCR that was performed by using a pCtB1 vector (GenBank Accession Number KJ922019) as a template and a primer set of a T7 primer and a T3 primer as primers. These DNA fragments, i.e., Fragments 4, 5, and 6, were combined together, and then, subjected to PCR using a primer set of SEQ ID NOS: 33 and 36 as primers, so as to obtain a 2,621 bp DNA fragment, which is a DNA fragment used to substitute a URA3 terminator BLAST for the GPD1 gene.

Transformation of the DNA fragment occurred in the MD1002 strain, and then, strains grown on a minimal medium without containing uracil (SD-URA; Yeast Nitrogen Base 6.7 g, Synthetic Drop-out without uracil 1.92 g, D-glucose 20 g, Bacto Agar 20 g/L) were selected therefrom. Among the selected strains, a strain having identification of a 2,860 bp DNA fragment was obtained by PCR that was performed by using a primer set of SEQ ID NOS: 37 and 38, wherein the primer set had identification of a 2,160 bp DNA fragment in the wild-type strain or the MD1002 strain. The obtained strain was subjected to a seed culture for one day in an YPD culture medium YPD (Yeast Extract 10 g, Bacto Peptone 20 g, D-glucose 20 g/L). Afterwards, colonies were spread on a 5-FOA culture medium (Yeast Nitrogen Base 6.7 g, Synthetic Drop-out without uracil 1.92 g, uracil 0.1 g, D-glucose 20 g, 5-fluoroorotic acid 1 g, Bacto Agar 20 g/L) to select strains that were grown and developed therefrom. Among the selected strains, PCR was performed again by using a primer set of SEQ ID NOS: 37 and 38, so as to obtain a strain having identification of a 1,466 bp DNA, and that is, a *S. cerevisiae* CEN.PK2-1 D stain (Δpdc1 Δgpd1) (hereinafter, referred to as 'MD1228 strain') was obtained.

1.3: Manufacture of Strain Including cyb2 Deletion

A 355 bp DNA (hereinafter, referred to as 'Fragment 7') was obtained as an amplification product by PCR that was performed by using the genome DNA of the *S. cerevisiae* CEN.PK2-1 D wild-type strain as a template and a primer set of SEQ ID NOS: 39 and 40 as primers. A 378 bp DNA fragment (hereinafter, referred to as 'Fragment 8') was obtained as an amplification product by PCR that was performed by using the genome DNA of the *S. cerevisiae* CEN.PK2-1D wild-type strain as a template and a primer set of SEQ ID NOS: 41 and 42 as primers. A 1,955 bp DNA fragment (hereinafter, referred to as 'Fragment 9') was obtained as an amplification product by PCR that was performed by using a pCtB1 vector (GenBank Accession Number KJ922019) as a template and a primer set of a T7 primer and a T3 primer as primers. These DNA fragments, i.e., Fragments 7, 8, and 9, were combined together, and then, subjected to PCR using a primer set of SEQ ID NOS:

39 and 42, so as to obtain a 2,630 bp DNA fragment, which is a DNA fragment used to substitute a URA3 terminator BLAST for the CYB2 gene.

Transformation of the DNA fragment occurred in the MD1128 strain, and then, strains grown on a minimal medium without containing uracil (SD-URA; Yeast Nitrogen Base 6.7 g, Synthetic Drop-out without uracil 1.92 g, D-glucose 20 g, Bacto Agar 20 g/L) were selected therefrom. Among the selected strains, a strain having identification of a 2,891 bp DNA was obtained by PCR that was performed by using a primer set of SEQ ID NOS: 43 and 44, wherein the primer set had identification of a 2,676 bp DNA in the MD1002 strain or the MD1228 strain. The obtained strain was subjected to a seed culture for one day in an YPD culture medium YPD (Yeast Extract 10 g, Bacto Peptone 20 g, D-glucose 20 g/L). Afterwards, colonies were spread on a 5-FOA culture medium (Yeast Nitrogen Base 6.7 g, Synthetic Drop-out without uracil 1.92 g, uracil 0.1 g, D-glucose 20 g, 5-fluoroorotic acid 1 g, Bacto Agar 20 g/L) to select strains that were grown and developed therefrom. Among the selected strains, PCR was performed again by using a primer set of SEQ ID NOS: 43 and 44, so as to obtain a strain having identification of a 1,497 bp DNA, and that is, a *S. cerevisiae* CEN.PK2-1 D stain (Δpdc1, Δgpd1, Δcyb2) (hereinafter, referred to as 'MD1258 strain') was obtained.

1.4: Manufacture of Strain Including dld1 Deletion

A 366 bp DNA (hereinafter, referred to as 'Fragment 10') was obtained as an amplification product by PCR that was performed by using the genome DNA of the *S. cerevisiae* CEN.PK2-1 D wild-type strain as a template and a primer set of SEQ ID NOS: 45 and 46 as primers. A 365 bp DNA fragment (hereinafter, referred to as 'Fragment 11') was obtained as an amplification product by PCR that was performed by using the genome DNA of the *S. cerevisiae* CEN.PK2-1D wild-type strain as a template and a primer set of SEQ ID NOS: 47 and 48 as primers. A 1,955 bp DNA fragment (hereinafter, referred to as 'Fragment 12') was obtained as an amplification product by PCR that was performed by using a pCtB1 vector (GenBank Accession Number KJ922019) as a template and a primer set of a T7 primer and a T3 primer as primers. These DNA fragments, i.e., Fragments 10, 11, and 12, were combined together, and then, subjected to PCR using a primer set of SEQ ID NOS: 45 and 48, so as to obtain a 2,628 bp DNA fragment, which is a DNA fragment used to substitute a URA3 terminator BLAST for the DLD1 gene.

Transformation of the DNA fragment occurred in the MD1258 strain, and then, strains grown on a minimal medium without containing uracil (SD-URA; Yeast Nitrogen Base 6.7 g, Synthetic Drop-out without uracil 1.92 g, D-glucose 20 g, Bacto Agar 20 g/L) were selected therefrom. Among the selected strains, a strain having identification of a 2,891 bp DNA was obtained by PCR that was performed by using a primer set of SEQ ID NOS: 49 and 50, wherein the primer set had identification of a 3,209 bp DNA in the wild-type strain, the MD1002 strain, the MD1228 strain, or the MD1258 strain. The obtained strain was subjected to a seed culture for one day in an YPD culture medium YPD (Yeast Extract 10 g, Bacto Peptone 20 g, D-glucose 20 g/L). Afterwards, colonies were spread on a 5-FOA culture medium (Yeast Nitrogen Base 6.7 g, Synthetic Drop-out without uracil 1.92 g, uracil 0.1 g, D-glucose 20 g, 5-fluoroorotic acid 1 g, Bacto Agar 20 g/L) to select strains that were grown and developed therefrom. Among the selected strains, PCR was performed again by using a primer set of SEQ ID NOS: 49 and 50, so as to obtain a strain having identification of a 41,815 bp DNA fragment, and that is, a *S. cerevisiae* CEN.PK2-1D strain (Δpdc1, Δgpd1, Δcyb2, Δdld1) (hereinafter, referred to as 'MD1257 strain') was obtained.

1.5: Manufacture of Vector for LDH Overexpression

Figure 2:
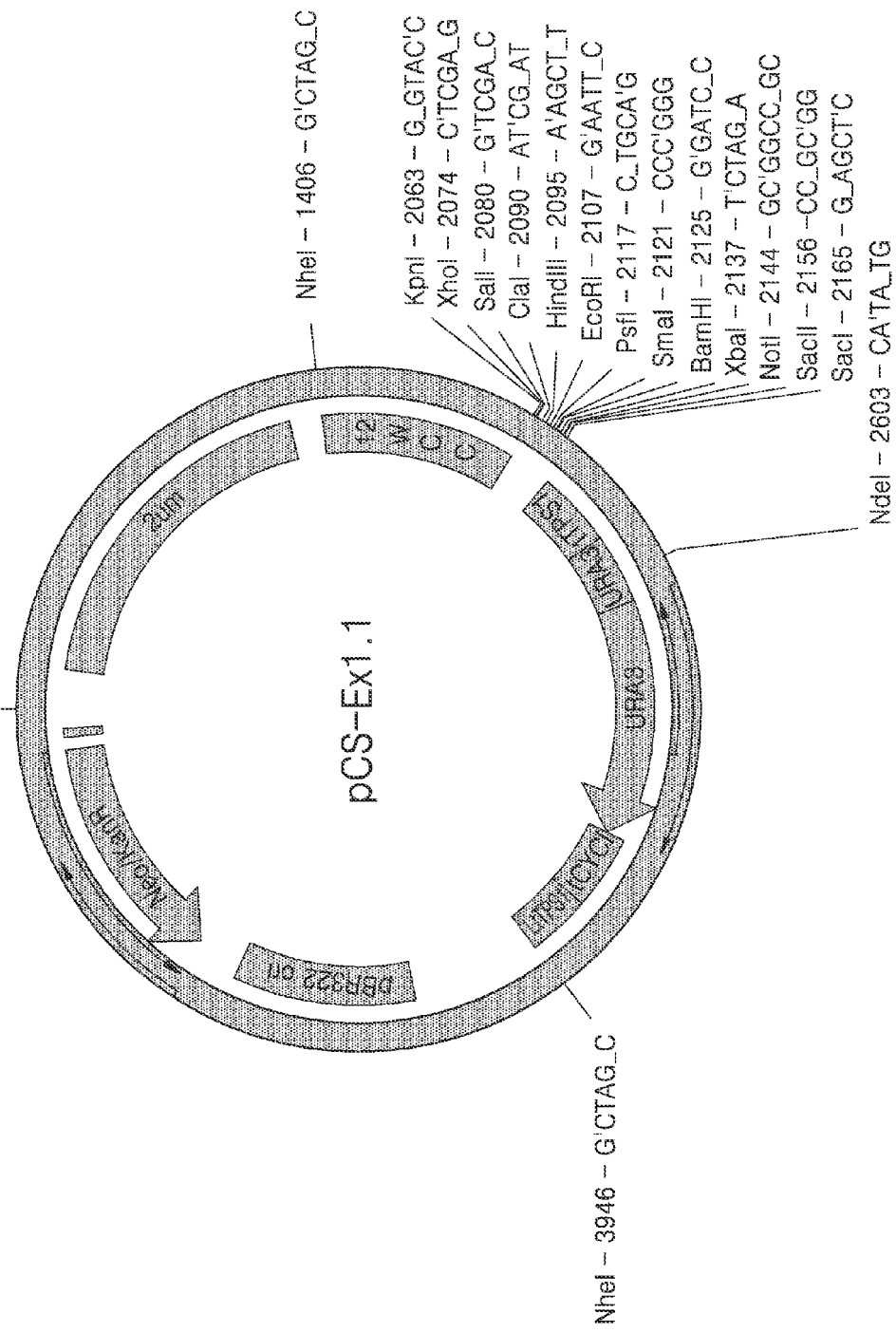
FIG. 2 is a vector map of a pCS-Ex1.1 vector.

A 1,605 bp DNA fragment including a CCW12 promoter was obtained as an amplification product by PCR that was performed by using the genome DNA of the *S. cerevisiae* CEN.PK2-1 D wild-type strain as a template and a primer set of SEQ ID NOS: 51 and 52 as primers. The DNA fragment was combined with a pCtB1 vector treated with KpnI, and cloned by using an In-fusion kit, so as to obtain a pCtB1-CCW12 vector (hereinafter, referred to as 'MD0922 vector'), which is a dual-purpose expression vector. The MD0922 vector was treated with KpnI and SacI, combined with a DNA fragment of the LDH gene derived that was derived from *Bos Taurus* (hereinafter, referred to as 'BtLDH') and synthesized as SEQ ID NO: 18, and cloned to a pCS-Ex1.1 vector by using an In-fusion kit, so as to obtain a pCS-Ex1.1 BtLDH vector (hereinafter, referred to as 'MD1188' vector), which is a dual-purpose vector for the overexpression of the LDH gene in yeast cell. The BtLDH gene was set to involve transcription in the presence of the CCW12 promoter. FIG. 2 is a view of a pCS-Ex1.1 vector.

1.6: Manufacture of Strain Including Adh1 Deletion and Having Capability of Producing Lactate A 333 bp DNA fragment (hereinafter, referred to as 'Fragment 13') was obtained as an amplification product by PCR that was performed by using the genome DNA of the *S. cerevisiae* CEN.PK2-1D wild-type strain as a template and a primer set of SEQ ID NOS: 53 and 54 as primers. A 397 bp DNA fragment (hereinafter, referred to as 'Fragment 14') was obtained as an amplification product by PCR that was performed by using the genome DNA of the *S. cerevisiae* CEN.PK2-1 D wild-type strain as a template and a primer set of SEQ ID NOS: 55 and 56 as primers. A 4,422 bp DNA fragment (hereinafter, referred to as 'Fragment 15') was obtained as an amplification product by PCR that was performed by using the MD1188 vector as a template and a primer set of a T7 primer and a T3 primer as primers. These DNA fragments, i.e., Fragments 12, 14, and 15, were combined together, and then, subjected to PCR using a primer set of SEQ ID NOS: 53 and 56, so as to obtain a 5,094 bp DNA fragment, which is a DNA fragment used to substitute a CCW12 promoter-BtLDH gene-TPS1 terminator-URA3 terminator BLAST for the ADH1 gene.

Transformation of the DNA fragment occurred in the MD1257 strain, and then, strains grown on a minimal medium without containing uracil (SD-URA; Yeast Nitrogen Base 6.7 g, Synthetic Drop-out without uracil 1.92 g, D-glucose 20 g, Bacto Agar 20 g/L) were selected therefrom. Among the selected strains, a strain having identification of a 5276 bp DNA was obtained by PCR that was performed by using a primer set of SEQ ID NOS: 57 and 58, wherein the primer set had identification of a 1,918 bp DNA in the wild-type strain, the MD1002 strain, the MD1228 strain, or the MD1258 strain. The obtained strain was subjected to a seed culture for one day in an YPD culture medium YPD (Yeast Extract 10 g, Bacto Peptone 20 g, D-glucose 20 g/L). Afterwards, colonies were spread on a 5-FOA culture medium (Yeast Nitrogen Base 6.7 g, Synthetic Drop-out without uracil 1.92 g, uracil 0.1 g, D-glucose 20 g, 5-fluoroorotic acid 1 g, Bacto Agar 20 g IL) to select strains that were grown and developed therefrom. Among the selected strains, PCR was performed again by using a primer set of SEQ ID NOS: 57 and 58, so as to obtain a strain having identification of a 3,882 bp DNA fragment, and that is, a *S. cerevisiae* CEN.PK2-1D strain (Δpdc1, Δgpd1, Δcyb2, Δdld1, Δadh1::Btldh) (hereinafter, referred to as 'MD1304 strain') was obtained.

Example 2: Manufacture of Strain for Overexpression of EDC2

2.1: Manufacture of Vector for Overexpression of EDC2

In order to overexpress the EDC2 gene in the MD1304 strain having capability of producing lactate, a vector for overexpression of EDC2 was manufactured. Here, a 479 bp DNA fragment including the EDC2 gene was obtained as an amplification product by PCR that was performed by using the genome DNA of the S. cerevisiae CEN.PK2-1 D wild-type strain as a template and a primer set of SEQ ID NOS: 59 and 60 as primers. The DNA fragment was combined with a DNA of a pRS426GPD vector treated with XbaI and XhoI to carry out cloning in the pRS426GPD vector by using an In-fusion kit, so as to obtain a pRS426GPD EDC2 vector as a vector for overexpression of EDC2. Afterwards, a 1,168 bp DNA fragment was obtained by PCR that was performed by using a primer set of SEQ ID NOS: 61 and 62 as primers from the pRS426GPD EDC2 vector. The DNA fragment was used to clone the GPD promoter-EDC2 gene to pCtB1. The DNA fragment was combined with DNA of the pCtB1 vector treated with KpnI and SacI, and then, cloned to the pCS-Ex1 by using an In-fusion kit, so as to obtain a MD1152 vector (i.e., pCS-Ex1 EDC2 vector), which is a dual-purpose vector for overexpression of EDC2. FIG. 3 is a view of a pCS-Ex1 vector. Here, the EDC2 gene was set to involve transcription in the presence of the GPD promoter.

2.2: Manufacture of Strain for Overexpression of EDC2 Overexpression and Manufacture of Control Strain In order to overexpress the EDC2 gene in the MD1304 strain having capability of producing lactate, an EDC2 overexpression gene cassette was inserted by being substituted with a PDC6 gene having no known gene function. A 3,057 bp DNA was obtained as an amplification product by PCR that was performed by using a MD1152 vector, which is a dual-purpose vector for overexpression of EDC2, as a template and a primer set of SEQ ID NOS: 63 and 64 as primers. That is, the DNA fragment was used to substitute the PDC6 for GPD promoter-EDC2-TPS1 terminator-URA3 terminator BLAST.

Transformation of the DNA fragment occurred in the S. cerevisiae CEN.PK2-1 D wild-type strain, and then, strains grown on a minimal medium without containing uracil (SD-URA; Yeast Nitrogen Base 6.7 g, Synthetic Drop-out without uracil 1.92 g, D-glucose 20 g, Bacto Agar 20 g/L) were selected therefrom. Among selected strains, a strain having identification of a 3,429 bp DNA fragment was obtained by PCR that was performed by using a primer set of SEQ ID NOS: 65 and 66, wherein the primer set had identification of a 2,300 bp DNA fragment in the wild-type strain, and that is, a S. cerevisiae CEN.PK2-1D stain (Δpdc1, Δgpd1, Δcyb2, Δdld1, Δadh1::Btldh, Δpdc6::EDC2) (hereinafter, referred to as 'MD1304/EDC2 strain') was obtained.

In order to manufacture a control strain, a 2,029 bp DNA fragment was obtained as an amplification product by PCR that was performed by using an empty pCtB1 vector as a template and a primer set of SEQ ID NOS: 63 and 64 as primers. Transformation of the DNA fragment occurred in the S. cerevisiae CEN.PK2-1D wild-type strain, and then, strains grown on a minimal medium without containing uracil (SD-URA; Yeast Nitrogen Base 6.7 g, Synthetic Drop-out without uracil 1.92 g, D-glucose 20 g, Bacto Agar 20 g/L) were selected therefrom. Among the selected strains, a strain having identification of a 2,301 bp DNA fragment was obtained from the wild-type strain by PCR that was performed by using a primer set of SEQ ID NOS: 65 and 66, wherein the primer set had identification of a 2,300 bp DNA fragment in the wild-type strain, and that is, a S. cerevisiae CEN.PK2-1D strain (Δpdc1, Δgpd1, Δcyb2, Δdld1, Δadh1::Btldh, Δpdc6) (hereinafter, referred to as 'MD1304/Δpdc6 strain') was obtained.

Example 3: Evaluation of Capability of Producing Lactate of Strain for Overexpression of EDC2

In order to evaluate effects of the overexpression of the EDC2 gene on a strain's capability of producing lactate, a typical batch flask test was carried out. Here, the MD1304/Δpdc6 strain and the MD1304/EDC2 strain under the exponential-growth phase were collected and inoculated into a YPD8 culture medium (Yeast Extract 10 g, Bacto Peptone 20 g, D-Glucose 80 g/1 L), which is a test medium for the batch flask test, thereby achieving optical density (OD) of 4.0 in the cell concentration of 600 nm. The cell-medium mixture was put in an incubator under microaerobic conditions including humidity of 95% or above and maintaining oxygen concentration of 2.5%, and then, the cell-medium mixture was sufficiently stirred and cultured at a temperature of 30° C.

As shown in Table 1 below, the results show that the MD1304/EDC2 strain where the EDC2 was overexpressed had better capability of producing lactate and greater lactate yields than those of the control group, i.e., the MD1304/Δpdc6 strain.

TABLE 1

| Strain | | 0 hour | 20 hours | 40 hours | 71 hours |
|---|---|---|---|---|---|
| MD1304/Δ pdc 6 | $OD_{600}$ | 3.97 ± 0.01 | 7.85 ± 0.27 | 10.96 ± 0.25 | 11.64 ± 0.18 |
| | D-glucose (g/L) | 84.8 ± 2.7 | 52.9 ± 1.2 | 40.5 ± 1.6 | 38.9 ± 0.8 |
| | L-lactate (g/L) | 0.2 ± 0.1 | 17.7 ± 0.5 | 25.2 ± 0.6 | 25.5 ± 0.7 |
| | Yield (g/g %) | — | 55 ± 3.7 | 56.6 ± 3.0 | 55.2 ± 1.4 |
| MD1304/EDC2 | $OD_{600}$ | 4.04 ± 0.10 | 6.89 ± 0.23 | 9.17 ± 0.98 | 10.91 ± 0.48 |
| | D-glucose (g/L) | 84.8 ± 2.7 | 50.8 ± 1.5 | 35.9 ± 1.6 | 25.2 ± 0.3 |
| | L-lactate (g/L) | 0.2 ± 0.1 | 21.3 ± 0.3 | 31.2 ± 0.9 | 35.4 ± 0.2 |
| | Yield (g/g %) | — | 62.1 ± 2.0 | 63.5 ± 3.1 | 59.1 ± 0.6 |

TABLE 1-continued

| Strain | | 0 hour | 20 hours | 40 hours | 71 hours |
|---|---|---|---|---|---|
| Δ (EDC2) | $OD_{600}$ | — | −12.2% | −16.3% | −6.3% |
| | D-glucose (g/L) | — | +6.6% | +10.6% | +29.7% |
| | L-lactate (g/L) | — | +20.4 % | +24.1% | +38.8% |
| | Yield (g/g %) | — | +12.9% | +12.2% | +7.1% |

* Average ± S.D (n = 3)

In Table 1, the measured $OD_{600}$, D-glucose, L-lactate, and yields in the Δ (EDC2) showed increased values of the MD1304/EDC2 associated with increased activity of the EDC2, as compared with those of the MD1304/Δ pdc6.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A genetically engineered yeast cell that produces lactate, wherein the genetically engineered yeast cell comprises a genetic modification that increases copy number of a polynucleotide encoding an enhancer of mRNA-decapping (EDC) protein as compared to the same yeast cell without the genetic modification that increases copy number, wherein the genetically modified yeast cell comprises an exogenous polynucleotide encoding a lactate dehydrogenase, and wherein the genetically modified yeast cell comprises a disruption mutation of a chromosomal gene encoding a polypeptide that converts pyruvate to acetaldehyde.

2. The genetically engineered yeast cell of claim 1, wherein the genetic modification that increases copy number is an exogenous promoter that is operably linked to the polynucleotide encoding the EDC protein.

3. The genetically engineered yeast cell of claim 1, wherein the genetic modification that increases copy number is an exogenous polynucleotide encoding the EDC protein.

4. The genetically engineered yeast cell of claim 1, wherein the EDC protein is an EDC1 protein or an EDC2 protein.

5. The genetically engineered yeast cell of claim 4, wherein the EDC2 protein comprises an amino acid sequence having 90% or more sequence identity with the amino acid sequence of SEQ ID NO: 1 and has mRNA-decapping enhancer activity.

6. The genetically engineered yeast cell of claim 4, wherein the EDC2 protein comprises an amino acid sequence having 95% or more sequence identity with the amino acid sequence of SEQ ID NO: 1 and has mRNA-decapping enhancer activity.

7. The genetically engineered yeast cell of claim 1, wherein the genetically engineered yeast cell belongs to the Saccharomyces genus, the Kluyveromyces genus, the Candida genus, the Pichia genus, the Issatchenkia genus, the Debaryomyces genus, the Zygosaccharomyces genus, the Shizosaccharomyces genus, or the Saccharomycopsis genus.

8. The genetically engineered yeast cell of claim 1, wherein the genetically engineered yeast cell is a Saccharomyces cerevisiae yeast cell.

9. The genetically engineered yeast cell of claim 1, wherein the genetically engineered yeast cell produces lactate under anaerobic, aerobic or microaerobic conditions.

10. The genetically engineered yeast cell of claim 1, wherein the lactate dehydrogenase comprises an amino acid sequence having 95% or more sequence identity with the amino acid sequence of SEQ ID NO: 13, 14, 15, 16 or 17 and has lactate dehydrogenase activity.

11. The genetically engineered yeast cell of claim 1, wherein the genetically engineered yeast cell further comprises a disruption mutation of a chromosomal gene encoding a polypeptide that converts lactate to pyruvate, a chromosomal gene encoding a polypeptide that converts dehydroxy acetone phosphate (DHAP) to glycerol-3-phosphate, a chromosomal gene encoding a polypeptide that converts pyruvate to D-lactate, a chromosomal gene encoding a polypeptide that converts acetaldehyde to ethanol, or a combination thereof.

12. A method of producing the genetically engineered yeast cell of claim 1, the method comprising:
    transforming a yeast cell with a polynucleotide that encodes an EDC protein,
    transforming the yeast cell with a polynucleotide that encodes a lactate dehydrogenase, and
    disrupting a chromosomal gene encoding a polypeptide that converts pyruvate to acetaldehyde in the yeast cell, thereby producing the genetically engineered yeast cell.

13. The method of claim 12, further comprising disrupting a chromosomal gene encoding a polypeptide that converts lactate to pyruvate, a chromosomal gene encoding a polypeptide that converts dehydroxy acetone phosphate (DHAP) to glycerol-3-phosphate, a chromosomal gene encoding a polypeptide that converts pyruvate to D-lactate, a chromosomal gene encoding a polypeptide that converts acetaldehyde to ethanol, or a combination thereof.

14. The method of claim 12, wherein the yeast cell is a Saccharomyces cerevisiae yeast cell.

15. A method of producing lactate, the method comprising:
    culturing the genetically engineered yeast cell of claim 1 in a cell culture medium, whereby the genetically engineered yeast cell produces lactate.

16. The method of claim 15, further comprising collecting the lactate from the cell culture medium.

17. The method of claim 15, wherein the culturing of the genetically engineered yeast cell is performed under a microaerobic condition.

* * * * *